United States Patent
Biadatti et al.

(10) Patent No.: US 7,468,457 B2
(45) Date of Patent: Dec. 23, 2008

(54) LIGAND INHIBITORS OF THE RAR RECEPTORS, PROCESS FOR PREPARING SAME AND THERAPEUTIC/COSMETIC APPLICATIONS THEREOF

(75) Inventors: Thibaud Biadatti, Opio (FR); Pascal Collette, Le Cannet (FR)

(73) Assignee: Galderma Research & Development, Biot (FR)

( * ) Notice: Subject to any disclaimer, the term of this patent is extended or adjusted under 35 U.S.C. 154(b) by 467 days.

(21) Appl. No.: 10/991,510

(22) Filed: Nov. 19, 2004

(65) Prior Publication Data

US 2005/0131033 A1 Jun. 16, 2005

Related U.S. Application Data

(63) Continuation of application No. PCT/EP03/05554, filed on May 27, 2003.

(30) Foreign Application Priority Data

Jun. 4, 2002 (FR) .................. 02 06850

(51) Int. Cl.
| | |
|---|---|
| C07D 211/70 | (2006.01) |
| C07C 59/00 | (2006.01) |
| A61K 31/44 | (2006.01) |
| A01N 43/26 | (2006.01) |

(52) U.S. Cl. ............... 562/465; 546/315; 514/355; 514/467; 514/569

(58) Field of Classification Search .............. 562/465; 546/315; 514/355, 467, 569
See application file for complete search history.

(56) References Cited

U.S. PATENT DOCUMENTS

| 5,023,363 A | 6/1991 | Maignan et al. | |
|---|---|---|---|
| 6,103,762 A * | 8/2000 | Bernardon et al. | 514/544 |
| 6,346,546 B1 * | 2/2002 | Bernardon et al. | 514/532 |

FOREIGN PATENT DOCUMENTS

FR 2 764 604 A 12/1998

OTHER PUBLICATIONS

International Search Report corresponding to PCT/EP03/05554 issued on Nov. 3, 2003, 3 pages.

* cited by examiner

*Primary Examiner*—D. Margaret Seaman
*Assistant Examiner*—Nizal S Chandrakumar
(74) *Attorney, Agent, or Firm*—Buchanan, Ingersoll & Rooney, PC

(57) ABSTRACT

Novel biaryl compounds having the structural formula (I):

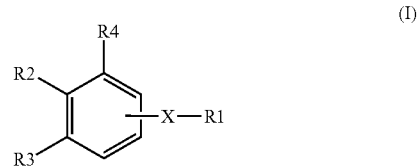

are useful in a variety of pharmaceutical applications, whether human or veterinary, and also in cosmetics.

16 Claims, 1 Drawing Sheet

LIGAND INHIBITORS OF THE RAR RECEPTORS, PROCESS FOR PREPARING SAME AND THERAPEUTIC/COSMETIC APPLICATIONS THEREOF

CROSS-REFERENCE TO PRIORITY/PCT/PROVISIONAL APPLICATIONS

This application claims priority under 35 U.S.C. § 119 of FR-02/06850, filed Jun. 4, 2002, and of provisional application Ser. No. 60/387,448, filed Jun. 11, 2002, and is a continuation of PCT/EP 03/05554, filed May 27, 2003 and designating the United States (published in the English language on Dec. 11, 2003 as WO 03/101928 A1), each hereby expressly incorporated by reference and each assigned to the assignee hereof.

BACKGROUND OF THE INVENTION

1. Technical Field of the Invention

The present invention relates to novel biaryl compounds, to the process for preparing same and to a variety of applications thereof in pharmaceutical compositions for use in human or veterinary medicine, or in cosmetic compositions.

2. Description of Background and/or Related and/or Prior Art

Compounds with activity of retinoid type (vitamin A and derivatives thereof) are widely described in the literature as having activity in cell differentiation and proliferation processes. These properties provide this class of compounds great potential in the treatment or prevention of numerous pathologies, and more particularly in dermatology and cancer. Many biological effects of retinoids are mediated by modulating the nuclear retinoic acid receptors (RAR), which are factors for transcribing ligand-dependent genes.

RAR receptors activate transcription by binding to DNA sequence elements, known as the RAR Element (RARE) response elements, in the form of a heterodimer with the retinoid X receptors (known as RXRs).

Three subtypes of human RARs have been identified and described: RARα, RARβ and RARγ.

The prior art contains a large number of chemical compounds with inhibitory activity on receptors of RAR type. Among the prior art documents that may be mentioned more particularly are EP-0,986,537 which describes heteroethynylenated compounds, U.S. Pat. No. 6,103,762 describing biaromatic compounds in which the aromatic nuclei are linked to a propynylene or allenylene divalent radical, U.S. Pat. No. 6,150,413, which describes triaromatic compounds, U.S. Pat. No. 5,723,499 which describes polycyclic aromatic compounds, and U.S. Pat. No. 6,214,878 which describes stilbene compounds. U.S. Pat. No. 6,218,128 itself describes a family of bicyclic or tricyclic molecules.

SUMMARY OF THE INVENTION

Novel biaryl compounds have now been developed that inhibit the retinoic acid receptors.

Thus, the present invention features novel biaryl compounds corresponding to the general formula below:

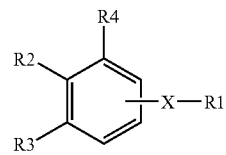

in which $R_1$ is a radical of formulae (a) to (c) below:

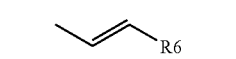

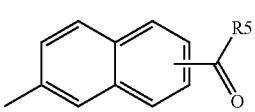

wherein $R_5$ and $R_6$ are as defined below; each of the radicals $R_2$ and $R_3$, which may be identical or different, is a hydrogen atom, a linear or branched alkyl radical of 1 to 6 carbon atoms, a radical $-OR_7$ or a radical $-NR_8R_9$, with the proviso that $R_2$ and $R_3$, may together form a 6-membered ring optionally substituted with linear or branched alkyl radicals of 1 to 3 carbon atoms; $R_7$, $R_8$ and $R_9$ are as defined below; $R_4$ is an aryl radical or a heterocyclic radical; X is $-CR_{10}R_{11}$, $-C=O$ or $-C=N-OR_{12}$; $R_{10}$, $R_{11}$ and $R_{12}$ are as defined below; $R_5$ is a hydroxyl, alkoxy, monoalkylamino or dialkylamino radical, or a linear or branched alkyl radical having from 1 to 6 carbon atoms; $R_6$ is one of the radicals below:

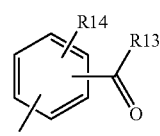

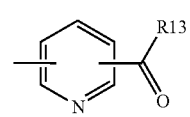

wherein $R_{13}$ and $R_{14}$ are as defined below; $R_7$ is a hydrogen atom, an alkyl radical having from 1 to 6 carbon atoms, or a benzyl radical optionally substituted with a linear or branched alkyl radical having from 1 to 6 carbon atoms, a halogen or a dialkylamino or alkoxy radical; $R_8$ and $R_9$, which may be identical or different, are each a hydrogen atom, a linear or branched alkyl radical having from 1 to 6 carbon atoms, or a benzyl radical; $R_{10}$ is a hydrogen atom or an $-OH$ radical; $R_{11}$ and $R_{12}$, which may be identical or different, are each a hydrogen atom or a linear or branched alkyl radical having from 1 to 6 carbon atoms; $R_{13}$ is a hydroxyl, alkoxy, monoalkylamino or dialkylamino radical; $R_{14}$ is a hydrogen atom, a hydroxyl radical or an amino radical, and the optical isomers and salts thereof obtained with a salt or a pharmaceutically acceptable base, and also mixtures of said compounds of formula (I).

BRIEF DESCRIPTION OF THE DRAWING

The FIGURE of Drawing illustrates various reaction mechanisms for the preparation of the compounds of the invention.

DETAILED DESCRIPTION OF BEST MODE AND SPECIFIC/PREFERRED EMBODIMENTS OF THE INVENTION

Figure 1:
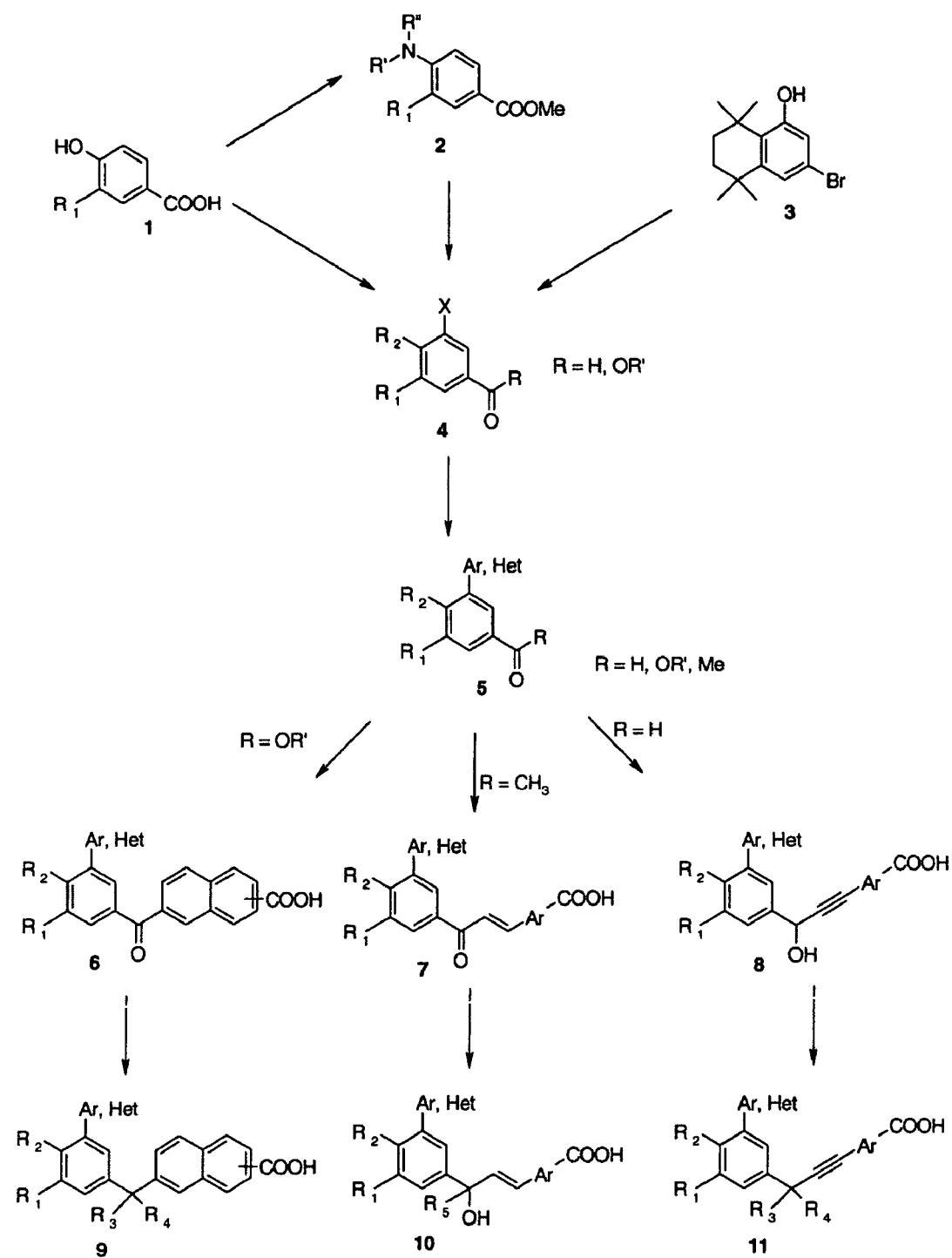

When the compounds according to the invention are in the form of a salt, it is preferably a salt of an alkali metal or alkaline-earth metal, or alternatively a zinc salt or salts of an organic amine.

According to the present invention:
the expression "alkyl radical having from 1 to 6 carbon atoms" preferably means methyl, ethyl, propyl, isopropyl, butyl, tert-butyl, pentyl or hexyl radicals.

The term "halogen atom" preferably means a fluorine, chlorine or bromine atom.

The term "alkoxy radical" means an oxygen atom substituted with a linear or branched alkyl radical having from 1 to 6 carbon atoms, and preferably a methoxy, ethoxy, propyloxy, isopropoxy, butoxy, tert-butoxy, pentoxy or hexyloxy radical.

The term "aryl radical" means a phenyl radical optionally substituted with one or more linear or branched alkyl radicals having from 1 to 6 carbon atoms, an alkoxy radical, a monoalkylamino radical, a dialkylamino radical or a halogen.

The term "monoalkylamino radical" means an amino radical substituted with a linear or branched alkyl radical having from 1 to 6 carbon atoms.

The term "dialkylamino radical" means an amino radical disubstituted with linear or branched alkyl radicals, which may be identical or different, having from 1 to 6 carbon atoms.

The term "heterocyclic radical" means a carbon-based ring of 5 to 8 carbon atoms interrupted with 1 or 2 hetero atoms selected from among sulfur, nitrogen and oxygen, and preferably a pyridine, morpholine, piperidine, piperazine or tetrahydropyridine N-substituted with an alkyl radical or with an alkylcarbamate in which the alkyl radical has from 1 to 4 carbon atoms.

Among the compounds corresponding to the general formula (I) above, mention may be made of the following, alone or in admixture:

4-[3-(6-Benzyloxy-5-tert-butyl-4'-methyl-3-biphenylyl)-3-hydroxy-1-propynyl]benzoic acid;
4-[(E)-3-(6-Benzyloxy-5-tert-butyl-4'-methyl-3-biphenylyl)-3-oxopropenyl]benzoic acid,
4-[(E)-3-(5-tert-Butyl-6-isobutoxy-4'-methyl-3-biphenylyl)-3-oxopropenyl]benzoic acid,
4-[(E)-3-(5-tert-Butyl-6-isobutoxy-4'-methyl-3-biphenylyl)-3-hydroxypropenyl]benzoic acid,
4-[3-Hydroxy-3-(5,5,8,8-tetramethyl-4-p-tolyl-5,6,7,8-tetrahydro-2-naphthyl)-1-propynyl]benzoic acid,
4-{3-[4-(4-tert-Butylphenyl)-5,5,8,8-tetramethyl-5,6,7,8-tetrahydro-2-naphthyl]-3-hydroxy-1-propynyl}benzoic acid,
4-{(E)-3-[4-(4-tert-Butylphenyl)-5,5,8,8-tetramethyl-5,6,7,8-tetrahydro-2-naphthyl]-3-oxopropenyl}benzoic acid,
4-[(E)-3-Oxo-3-(5,5,8,8-tetramethyl-4-p-tolyl-5,6,7,8-tetrahydro-2-naphthyl)propenyl]benzoic acid,
4-[(E)-3-Hydroxy-3-(5,5,8,8-tetramethyl-4-p-tolyl-5,6,7,8-tetrahydro-2-naphthyl)propenyl]benzoic acid,
4-{(E)-3-[4-(4-tert-Butylphenyl)-5,5,8,8-tetramethyl-5,6,7,8-tetrahydro-2-naphthyl]-3-hydroxypropenyl}-2-hydroxybenzoic acid,
4-{(E)-3-[4-(4-tert-Butylphenyl)-5,5,8,8-tetramethyl-5,6,7,8-tetrahydro-2-naphthyl]-3-oxopropenyl}-2-hydroxybenzoic acid,
4-{3-[4-(4-tert-Butylphenyl)-5,5,8,8-tetramethyl-5,6,7,8-tetrahydro-2-naphthyl]-3-hydroxy-1-propynyl}-2-hydroxybenzoic acid,
2-Hydroxy-4-[(E)-3-hydroxy-3-(5,5,8,8-tetramethyl-4-p-tolyl-5,6,7,8-tetrahydro-2-naphthyl)propenyl]benzoic acid,
2-Hydroxy-4-[(E)-3-oxo-3-(5,5,8,8-tetramethyl-4-p-tolyl-5,6,7,8-tetrahydro-2-naphthyl)propenyl]benzoic acid,
2-Hydroxy-4-[3-hydroxy-3-(5,5,8,8-tetramethyl-4-p-tolyl-5,6,7,8-tetrahydro-2-naphthyl]-1-propynyl]benzoic acid,
4-{(E)-3-[4-(4-Dimethylaminophenyl)-5,5,8,8-tetramethyl-5,6,7,8-tetrahydro-2-naphthyl]-3-hydroxypropenyl}benzoic acid,
4-{(E)-3-[4-(4-Dimethylaminophenyl)-5,5,8,8-tetramethyl-5,6,7,8-tetrahydro-2-naphthyl]-3-oxopropenyl}benzoic acid,
4-{3-[4-(4-Dimethylaminophenyl)-5,5,8,8-tetramethyl-5,6,7,8-tetrahydro-2-naphthyl]-3-hydroxy-1-propynyl}benzoic acid,
4-{(E)-3-[4-(4-Dimethylaminophenyl)-5,5,8,8-tetramethyl-5,6,7,8-tetrahydro-2-naphthyl]-3-hydroxypropenyl}-2-hydroxybenzoic acid,
4-{(E)-3-[4-(4-Dimethylaminophenyl)-5,5,8,8-tetramethyl-5,6,7,8-tetrahydro-2-naphthyl]-3-oxopropenyl}-2-hydroxybenzoic acid,
4-{3-[4-(4-Dimethylaminophenyl)-5,5,8,8-tetramethyl-5,6,7,8-tetrahydro-2-naphthyl]-3-hydroxy-1-propynyl}-2-hydroxybenzoic acid,
4-{(E)-3-[4-(4-Diethylaminophenyl)-5,5,8,8-tetramethyl-5,6,7,8-tetrahydro-2-naphthyl]-3-hydroxypropenyl}benzoic acid,
4-{(E)-3-[4-(4-Diethylaminophenyl)-5,5,8,8-tetramethyl-5,6,7,8-tetrahydro-2-naphthyl]-3-oxopropenyl}benzoic acid,
4-{3-[4-(4-Diethylaminophenyl)-5,5,8,8-tetramethyl-5,6,7,8-tetrahydro-2-naphthyl]-3-hydroxy-1-propynyl}benzoic acid,
4-{(E)-3-[4-(4-Diethylaminophenyl)-5,5,8,8-tetramethyl-5,6,7,8-tetrahydro-2-naphthyl]-3-hydroxypropenyl}-2-hydroxybenzoic acid,
4-{(E)-3-[4-(4-Diethylaminophenyl)-5,5,8,8-tetramethyl-5,6,7,8-tetrahydro-2-naphthyl]-3-oxopropenyl}-2-hydroxybenzoic acid,
4-{3-[4-(4-Diethylaminophenyl)-5,5,8,8-tetramethyl-5,6,7,8-tetrahydro-2-naphthyl]-3-hydroxy-1-propynyl}-2-hydroxybenzoic acid,
4-{(E)-3-[4-(4-Methoxyphenyl)-5,5,8,8-tetramethyl-5,6,7,8-tetrahydro-2-naphthyl]-3-hydroxypropenyl}benzoic acid,
4-{(E)-3-[4-(4-Methoxyphenyl)-5,5,8,8-tetramethyl-5,6,7,8-tetrahydro-2-naphthyl]-3-oxopropenyl}benzoic acid,
4-{3-[4-(4-Methoxyphenyl)-5,5,8,8-tetramethyl-5,6,7,8-tetrahydro-2-naphthyl]-3-hydroxy-1-propynyl}benzoic acid,
4-{(E)-3-[4-(4-Methoxyphenyl)-5,5,8,8-tetramethyl-5,6,7,8-tetrahydro-2-naphthyl]-3-hydroxypropenyl}-2-hydroxybenzoic acid,
4-{(E)-3-[4-(4-Methoxyphenyl)-5,5,8,8-tetramethyl-5,6,7,8-tetrahydro-2-naphthyl]-3-oxopropenyl}-2-hydroxybenzoic acid,
4-{3-[4-(4-Methoxyphenyl)-5,5,8,8-tetramethyl-5,6,7,8-tetrahydro-2-naphthyl]-3-hydroxy-1-propynyl}-2-hydroxybenzoic acid,
4-{(E)-3-Hydroxy-3-(5,5,8,8-tetramethyl-4-pyrid-4-yl-5,6,7,8-tetrahydro-2-naphthyl)propenyl]benzoic acid, 4-{(E)-3-Oxo-3-(5,5,8,8-tetramethyl-4-pyrid-4-yl-5,6,7,8-tetrahydro-2-naphthyl)propenyl]benzoic acid,
4-[3-Hydroxy-3-(5,5,8,8-tetramethyl-4-pyrid-4-yl-5,6,7,8-tetrahydro-2-naphthyl)-1-propynyl]benzoic acid,
2-Hydroxy-4-[(E)-3-hydroxy-3-(5,5,8,8-tetramethyl-4-pyrid-4-yl-5,6,7,8-tetrahydro-2-naphthyl)propenyl]benzoic acid,
2-Hydroxy-1-[(E)-3-oxo-3-(5,5,8,8-tetramethyl-4-pyrid-4-yl-5,6,7,8-tetrahydro-2-naphthyl)propenyl]benzoic acid,
2-Hydroxy-4-[3-hydroxy-3-(5,5,8,8-tetramethyl-4-pyrid-4-yl-5,6,7,8-tetrahydro-2-naphthyl)-1-propynyl]benzoic acid,
4-{(E)-3-Hydroxy-3-(5,5,8,8-tetramethyl-4-(1-methyl-1,2,3,6-tetrahydro-4-pyridyl)-5,6,7,8-tetrahydro-2-naphthyl]propenyl}benzoic acid,
4-[(E)-3-Oxo-3-(5,5,8,8-tetramethyl-4-(1-methyl-1,2,3,6-tetrahydro-4-pyridyl)-5,6,7,8-tetrahydro-2-naphthyl)propenyl]benzoic acid,
4-[3-Hydroxy-3-(5,5,8,8-tetramethyl-4-(1-methyl-1,2,3,6-tetrahydro-4-pyridyl)-5,6,7,8-tetrahydro-2-naphthyl)-1-propynyl]benzoic acid,
2-Hydroxy-4-[(E)-3-hydroxy-3-(5,5,8,8-tetramethyl-4-(1-methyl-1,2,3,6-tetrahydro-4-pyridyl)-5,6,7,8-tetrahydro-2-naphthyl)propenyl]benzoic acid,
2-Hydroxy-4-[(E)-3-oxo-3-(5,5,8,8-tetramethyl-4-(1-methyl-1,2,3,6-tetrahydro-4-pyridyl)-5,6,7,8-tetrahydro-2-naphthyl)propenyl]benzoic acid,
2-Hydroxy-4-[3-hydroxy-3-(5,5,8,8-tetramethyl-4-(1-methyl-1,2,3,6-tetrahydro-4-pyridyl)-5,6,7,8-tetrahydro-2-naphthyl)-1-propynyl]benzoic acid,
4-{(E)-3-Hydroxy-3-[5,5,8,8-tetramethyl-4-(1-isopropyl-1,2,3,6-tetrahydro-4-pyridyl)-5,6,7,8-tetrahydro-2-naphthyl]propenyl}benzoic acid,
4-[(E)-3-Oxo-3-(5,5,8,8-tetramethyl-4-(1-isopropyl-1,2,3,6-tetrahydro-4-pyridyl)-5,6,7,8-tetrahydro-2-naphthyl)propenyl]benzoic acid,
4-[3-Hydroxy-3-(5,5,8,8-tetramethyl-4-(1-isopropyl-1,2,3,6-tetrahydro-4-pyridyl)-5,6,7,8-tetrahydro-2-naphthyl)-1-propynyl]benzoic acid,
2-Hydroxy-4-[(E)-3-hydroxy-3-(5,5,8,8-tetramethyl-4-(1-isopropyl-1,2,3,6-tetrahydro-4-pyridyl)-5,6,7,8-tetrahydro-2-naphthyl)propenyl]benzoic acid,
2-Hydroxy-4-[(E)-3-oxo-3-(5,5,8,8-tetramethyl-4-(1-isopropyl-1,2,3,6-tetrahydro-4-pyridyl)-5,6,7,8-tetrahydro-2-naphthyl)propenyl]benzoic acid,
2-Hydroxy-4-[3-hydroxy-3-(5,5,8,8-tetramethyl-4-(1-isopropyl-1,2,3,6-tetrahydro-4-pyridyl)-5,6,7,8-tetrahydro-2-naphthyl)-1-propynyl]benzoic acid,
4-{(E)-3-Hydroxy-3-(5,5,8,8-tetramethyl-4-(1-carboxyethyl-1,2,3,6-tetrahydro-4-pyridyl)-5,6,7,8-tetrahydro-2-naphthyl]propenyl}benzoic acid,
4-[(E)-3-Oxo-3-(5,5,8,8-tetramethyl-4-(1-carboxyethyl-1,2,3,6-tetrahydro-4-pyridyl)-5,6,7,8-tetrahydro-2-naphthyl)propenyl]benzoic acid,
4-[3-Hydroxy-3-(5,5,8,8-tetramethyl-4-(1-carboxyethyl-1,2,3,6-tetrahydro-4-pyridyl)-5,6,7,8-tetrahydro-2-naphthyl)-1-propynyl]benzoic acid,
2-Hydroxy-4-[(E)-3-hydroxy-3-(5,5,8,8-tetramethyl-4-(1-carboxyethyl-1,2,3,6-tetrahydro-4-pyridyl)-5,6,7,8-tetrahydro-2-naphthyl)propenyl]benzoic acid,
2-Hydroxy-4-[(E)-3-oxo-3-(5,5,8,8-tetramethyl-4-(1-carboxyethyl-1,2,3,6-tetrahydro-4-pyridyl)-5,6,7,8-tetrahydro-2-naphthyl)propenyl]benzoic acid,
2-Hydroxy-4-[3-hydroxy-3-(5,5,8,8-tetramethyl-4-(1-carboxyethyl-1,2,3,6-tetrahydro-4-pyridyl)-5,6,7,8-tetrahydro-2-naphthyl)-1-propynyl]benzoic acid,
4-{(E)-3-Hydroxy-3-[4-(4-isopropyl-1-piperazinyl)-5,5,8,8-tetramethyl-5,6,7,8-tetrahydro-2-naphthyl]propenyl}benzoic acid,
4-{(E)-3-[4-(4-Isopropyl-1-piperazinyl)-5,5,8,8-tetramethyl-5,6,7,8-tetrahydro-2-naphthyl]-3-oxopropenyl}benzoic acid,
4-{3-Hydroxy-3-[4-(4-isopropyl-1-piperazinyl)-5,5,8,8-tetramethyl-5,6,7,8-tetrahydro-2-naphthyl]-1-propynyl}benzoic acid,
2-Hydroxy-4-{(E)-3-hydroxy-3-[4-(4-isopropyl-1-piperazinyl)-5,5,8,8-tetramethyl-5,6,7,8-tetrahydro-2-naphthyl]propenyl}benzoic acid,
2-Hydroxy-4-{(E)-3-[4-(4-isopropyl-1-piperazinyl)-5,5,8,8-tetramethyl-5,6,7,8-tetrahydro-2-naphthyl]-3-oxopropenyl}benzoic acid,
2-Hydroxy-4-{3-hydroxy-3-[4-(4-isopropyl-1-piperazinyl)-5,5,8,8-tetramethyl-5,6,7,8-tetrahydro-2-naphthyl]-1-propynyl}benzoic acid,
4-{(E)-3-Hydroxy-3-[4-(4-carboxyethyl-1-piperazinyl)-5,5,8,8-tetramethyl-5,6,7,8-tetrahydro-2-naphthyl]propenyl}benzoic acid,
4-{(E)-3-[4-(4-Carboxyethyl-1-piperazinyl)-5,5,8,8-tetramethyl-5,6,7,8-tetrahydro-2-naphthyl]-3-oxopropenyl}benzoic acid,
4-{3-Hydroxy-3-[4-(4-carboxyethyl-1-piperazinyl)-5,5,8,8-tetramethyl-5,6,7,8-tetrahydro-2-naphthyl]-1-propynyl}benzoic acid,
2-Hydroxy-4-{(E)-3-hydroxy-3-[4-(4-carboxyethyl-1-piperazinyl)-5,5,8,8-tetramethyl-5,6,7,8-tetrahydro-2-naphthyl]propenyl}benzoic acid,
2-Hydroxy-4-{(E)-3-[4-(4-carboxyethyl-1-piperazinyl)-5,5,8,8-tetramethyl-5,6,7,8-tetrahydro-2-naphthyl]-3-oxopropenyl}benzoic acid,
2-Hydroxy-4-{3-hydroxy-3-[4-(4-carboxyethyl-1-piperazinyl)-5,5,8,8-tetramethyl-5,6,7,8-tetrahydro-2-naphthyl]-1-propynyl}benzoic acid,
4-{(E)-3-Hydroxy-3-[4-(4-methyl-1-piperazinyl)-5,5,8,8-tetramethyl-5,6,7,8-tetrahydro-2-naphthyl]propenyl}benzoic acid,
4-{(E)-3-[4-(4-Methyl-1-piperazinyl)-5,5,8,8-tetramethyl-5,6,7,8-tetrahydro-2-naphthyl]-3-oxopropenyl}benzoic acid,
4-{3-Hydroxy-3-[4-(4-methyl-1-piperazinyl)-5,5,8,8-tetramethyl-5,6,7,8-tetrahydro-2-naphthyl]-1-propynyl}benzoic acid,
2-Hydroxy-4-{(E)-3-hydroxy-3-[4-(4-methyl-1-piperazinyl)-5,5,8,8-tetramethyl-5,6,7,8-tetrahydro-2-naphthyl]propenyl}benzoic acid,
2-Hydroxy-4-{(E)-3-[4-(4-methyl-1-piperazinyl)-5,5,8,8-tetramethyl-5,6,7,8-tetrahydro-2-naphthyl]-3-oxopropenyl}benzoic acid,
2-Hydroxy-4-{3-hydroxy-3-[4-(4-methyl-1-piperazinyl)-5,5,8,8-tetramethyl-5,6,7,8-tetrahydro-2-naphthyl]-1-propynyl}benzoic acid,
6-[1-(5,5,8,8-Tetramethyl-4-p-tolyl-5,6,7,8-tetrahydro-2-naphthyl)methanoyl]naphthalene-2-carboxylic acid,
6-[1-Hydroxy-1-(5,5,8,8-tetramethyl-4-p-tolyl-5,6,7,8-tetrahydro-2-naphthyl)methyl]naphthalene-2-carboxylic acid,
6-{1-[5,5,8,8-Tetramethyl-4-(4-methyl-1-piperazinyl)-5,6,7,8-tetrahydro-2-naphthyl]methanoyl}naphthalene-2-carboxylic acid,
6-{1-Hydroxy-1-[5,5,8,8-tetramethyl-4-(4-methyl-1-piperazinyl)-5,6,7,8-tetrahydro-2-naphthyl]methyl}naphthalene-2-carboxylic acid,
4-[(E)-3-(4-Benzyloxy-3-tert-butyl-5-piperid-1-ylphenyl)-3-hydroxypropenyl]benzoic acid, 4-[(E)-3-(4-Benzyloxy-3-tert-butyl-5-piperid-1-ylphenyl)-3-oxopropenyl]benzoic acid, 4-[3-(4-Benzyloxy-3-tert-butyl-5-piperid-1-ylphenyl)-3-hydroxy-1-propynyl]benzoic acid, 4-{(E)-3-[4-Benzyloxy-3-tert-butyl-5-(4-methyl-1-piperazinyl)phenyl]-3-hydroxypropenyl}benzoic acid, 4-{(E)-3-[4-Benzyloxy-3-tert-butyl-5-(4-methyl-1-piperazinyl)phenyl]-3-oxopropenyl}benzoic acid, 4-{3-[4-Benzyloxy-3-tert-butyl-5-(4-methyl-1-piperazinyl)phenyl]-3-hydroxy-1-propynyl}benzoic acid, 4-[(E)-3-[4-Benzyloxy-3-tert-butyl-5-(4-methyl-1-piperazinyl)phenyl]-3-hydroxypropenyl}-2-hydroxybenzoic acid, 4-{(E)-3-[4-Benzyloxy-3-tert-butyl-5-(4-methyl-1-piperazinyl)phenyl]-3-oxopropenyl}-2-hydroxybenzoic acid, 4-{3-[4-Benzyloxy-3-tert-butyl-5-(4-methyl-1-piperazinyl)phenyl]-3-hydroxy-1-propynyl}-2-hydroxybenzoic acid, 4-{(E)-3-[4-Benzylamino-3-tert-butyl-5-(4-methyl-1-piperazinyl)phenyl]-3-oxopropenyl}benzoic acid, 4-{(E)-3-[3-tert-Butyl-4-isobutylamino-5-(4-methyl-1-piperazinyl)phenyl]-3-oxopropenyl}benzoic acid, 4-{(E)-3-[4-(Benzylmethylamino)-3-tert-butyl-5-(4-methyl-1-piperazinyl)phenyl]-3-oxopropenyl}benzoic acid, 4-{(E)-3-[3-(5-tert-Butyl)-4-(isobutylmethylamino)-5-(4-methyl-1-piperazinyl)phenyl]-3-oxopropenyl}benzoic acid, 4-{(E)-3-[4-Benzylamino-3-tert-butyl-5-(4-methyl-1-piperazinyl)phenyl]-3-hydroxypropenyl}benzoic acid, 4-{(E)-3-[4-(Benzylmethylamino)-3-tert-butyl-5-(4-methyl-1-piperazinyl)phenyl]-3-hydroxypropenyl}benzoic acid, 4-{(E)-3-[3-tert-Butyl-4-isobutylamino-5-(4-methyl-1-piperazinyl)phenyl]-3-hydroxypropenyl}benzoic acid, 4-{(E)-3-[3-tert-Butyl-4-(isobutylmethylamino)-5-(4-methyl-1-piperazinyl)phenyl]-3-hydroxypropenyl}benzoic acid, 4-{3-[4-Benzylamino-3-tert-butyl-5-(4-methyl-1-piperazinyl)phenyl]-3-hydroxy-1-propynyl}benzoic acid, 4-{3-[4-(Benzylmethylamino)-3-tert-butyl-5-(4-methyl-1-piperazinyl)phenyl]-3-hydroxy-1-propynyl}benzoic acid, 4-{3-[3-tert-Butyl-4-isobutylamino-5-(4-methyl-1-piperazinyl)phenyl]-3-hydroxy-1-propynyl}benzoic acid, 4-{3-[3-tert-Butyl-4-(isobutylmethylamino)-5-(4-methyl-1-piperazinyl)phenyl]-3-hydroxy-1-propynyl}benzoic acid, 4-[(E)-3-(6-Benzylamino-5-tert-butyl-4'-methyl-3-biphenylyl)-3-oxopropenyl]benzoic acid, 4-[(E)-3-[6-(Benzylmethylamino)-5-tert-butyl-4'-methyl-3-biphenyl]-3-oxopropenyl}benzoic acid, 4-[(E)-3-(5-tert-Butyl-6-isobutylamino-4-methyl-3-biphenylyl)-3-oxopropenyl]benzoic acid, 4-{(E)-3-[5-tert-Butyl-6-(isobutylmethylamino)-4'-methyl-3-biphenylyl]-3-oxopropenyl}benzoic acid, 4-[(E)-3-(6-Benzylamino-5-tert-butyl-4'-methyl-3-biphenylyl)-3-hydroxypropenyl]benzoic acid, 4-{(E)-3-[6-(Benzylmethylamino)-5-tert-butyl-4'-methyl-3-biphenylyl]-3-hydroxypropenyl}benzoic acid, 4-[(E)-3-(5-tert-Butyl-6-isobutylamino-4'-methyl-3-biphenylyl)-3-hydroxypropenyl]benzoic acid, 4-{(E)-3-(5-tert-Butyl-6-(isobutylmethylamino)-4'-methyl-3-biphenylyl]-3-hydroxypropenyl}benzoic acid, 4-[3-(6-Benzylamino-5-tert-butyl-4'-methyl-3-biphenylyl)-3-hydroxy-1-propynyl]benzoic acid, 4-{3-[(6-Benzylmethylamino)-5-tert-butyl-4'-methyl-3-biphenylyl]-3-hydroxy-1-propynyl}benzoic acid, 4-[3-(5-tert-Butyl-6-isobutylamino-4'-methyl-3-biphenylyl)-3-hydroxy-1-propynyl]benzoic acid, 4-{3-[5-tert-Butyl-6-(isobutylmethylamino)-4'-methyl-3-biphenylyl]-3-hydroxy-1-propynyl}benzoic acid, 4-[(E)-3-(6-Dimethylamino-5-tert-butylmethyl-3-biphenylyl)-3-hydroxypropenyl]benzoic acid, 4-[(E)-3-(6-Dimethylamino-5-tert-butylmethyl-3-biphenylyl)-3-oxopropenyl]benzoic acid, 4-[(E)-3-(6-Dimethylamino-5-tert-butylmethyl-3-biphenylyl)-3-hydroxy-1-propynyl]benzoic acid, 4-[(E)-3-(6-Benzylamino-5,4'-di-tert-butyl-3-biphenylyl)-3-oxopropenyl]benzoic acid, 4-{(E)-3-[6-(Benzylmethylamino)-5,4'-di-tert-butyl-3-biphenylyl)-3-oxopropenyl}benzoic acid, 4-[(E)-3-(5,4'-di-tert-Butyl-6-isobutylamino-3-biphenylyl)-3-oxopropenyl]benzoic acid, 4-{(E)-3-(5,4'-di-tert-Butyl-6-(isobutylmethylamino)-3-biphenylyl]-3-oxopropenyl}benzoic acid, 4-[(E)-3-(6-Benzylamino-5,4'-di-tert-butyl-3-biphenylyl)-3-hydroxypropenyl]benzoic acid, 4-{(E)-3-[6-Benzylmethylamino)-5,4'-di-tert-butyl-3-biphenylyl]-3-hydroxypropenyl}benzoic acid, 4-[(E)-3-[5-tert-Butyl-6-isobutylamino-4'-methyl-3-biphenylyl)-3-hydroxypropenyl]benzoic acid, 4-{(E)-3-[5-tert-Butyl-6-(isobutylmethylamino)-4'-methyl-3-biphenylyl]-3-hydroxypropenyl}benzoic acid, 4-[3-(6-Benzylamino-5,4'-di-tert-butyl-3-biphenylyl)-3-hydroxy-1-propynyl]benzoic acid, 4-{3-[6-(Benzylmethylamino)-5,4'-di-tert-butyl-3-biphenylyl]-3-hydroxy-1-propynyl}benzoic acid, 4-[3-(5,4'-di-tert-Butyl-6-isobutylamino-3-biphenylyl)-3-hydroxy-1-propynyl]benzoic acid, 4-{3-[5,4'-di-tert-Butyl-6-(isobutylmethylamino)-3-biphenylyl]-3-hydroxy-1-propynyl}benzoic acid, 4-{(E)-3-[6-Dimethylamino-5,4'-di-tert-butyl-3-biphenylyl]-3-hydroxypropenyl}benzoic acid, 4-{(E)-3-[6-Dimethylamino-5,4'-di-tert-butyl-3-biphenylyl]-3-oxopropenyl}benzoic acid, 4-{3-[6-Dimethylamino-5,4'-di-tert-butyl-3-biphenylyl]-3-hydroxy-1-propynyl}benzoic acid, 4-[(E)-3-(6,4'-di-tert-Butyl-5-dimethylamino-3-biphenylyl)-3-hydroxypropenyl]benzoic acid, 4-[(E)-3-(6,4'-di-tert-Butyl-5-dimethylamino-3-biphenylyl)-3-oxopropenyl]benzoic acid, 4-[3-(6,4'-di-tert-Butyl-5-dimethylamino-3-biphenylyl)-3-hydroxy-1-propynyl]benzoic acid, 4-[(E)-3-(6-tert-Butyl-5-dimethylamino-4-methyl-3-biphenylyl)-3-hydroxypropenyl]benzoic acid, 4-[(E)-3-(6-tert-Butyl-5-dimethylamino-4'-methyl-3-biphenylyl)-3-oxopropenyl]benzoic acid, 4-[3-(6-tert-Butyl-5-dimethylamino-4'-methyl-3-biphenylyl)-3-hydroxy-1-propynyl]benzoic acid, 4-[(E)-3-(6,4'-di-tert-Butyl-5-isobutoxy-3-biphenylyl)-3-hydroxypropenyl]benzoic acid, 4-[(E)-3-(6,4'-di-tert-Butyl-5-isobutoxy-3-biphenylyl)-3-oxopropenyl]benzoic acid, 4-[3-(6,4'-di-tert-Butyl-5-isobutoxy-3-biphenylyl)-3-hydroxy-1-propynyl]benzoic acid, 4-[(E)-3-(6-tert-Butyl-5-isobutoxy-4'-methyl-3-biphenylyl)-3-hydroxypropenyl]benzoic acid, 4-[(E)-3-(6-tert-Butyl-5-isobutoxy-4'-methyl-3-biphenylyl)-3-oxopropenyl]benzoic acid, 4-[3-(6-tert-Butyl-5-isobutoxy-4'-methyl-3-biphenylyl)-3-hydroxy-1-propynyl]benzoic acid, 4-[(E)-3-(6,4'-di-tert-Butyl-5-benzyloxy-3-biphenylyl)-3-hydroxypropenyl]benzoic acid, 4-[(E)-3-(6,4'-di-tert-Butyl-5-benzyloxy-3-biphenylyl)-3-oxopropenyl]benzoic acid, 4-[3-(6,4'-di-tert-Butyl-5-benzyloxy-3-biphenylyl)-3-hydroxy-1-propynyl]benzoic acid, 4-[(E)-3-(6-tert-Butyl-5-benzyloxy-4'-methyl-3-biphenylyl)-3-hydroxypropenyl]benzoic acid, 4-[(E)-3-(6-tert-Butyl-5-benzyloxy-4'-methyl-3-biphenylyl)-3-oxopropenyl]benzoic acid, 4-[3-(6-tert-Butyl-5-benzyloxy-4'-methyl-3-biphenylyl)-3-hydroxy-1-propynyl]benzoic acid, 6-[3-Hydroxy-3-(5,5,8,8-tetramethyl-4-p-tolyl-5,6,7,8-tetrahydro-2-naphthyl)-1-propynyl]nicotinic acid, 6-{3-[4-(4-tert-Butylphenyl)-5,5,8,8-tetramethyl-5,6,7,8-tetrahydro-2-naphthyl]-3-hydroxy-1-propynyl}nicotinic acid, 6-[3-(6-Benzyloxy-5-tert-butyl-4'-methyl-3-biphenylyl)-3-hydroxy-1-propynyl]nicotinic acid, 6-[3-(5-tert-Butyl-6-isobutoxy-4'-methyl-3-biphenylyl)-3-hydroxy-1-propynyl]nicotinic acid, 6-[3-(6-Benzyloxy-5,4'-di-tert-butyl-3-biphenylyl)-3-hydroxy-1-propynyl]nicotinic acid, 6-[1-Hydroxyimino-1-(5,5,8,8-tetramethyl-4-p-tolyl-5,6,7,8-tetrahydro-2-naphthyl)methyl]-2-naphthalenecarboxylic acid, 6-[1-[4-(4-tert-Butylphenyl)-5,5,8,8-tetramethyl-5,6,7,8-tetrahydro-2-naphthyl]-1-hydroxyiminomethyl}-2-naphthalenecarboxylic acid, 6-{1-(5-tert-Butyl-6-isobutoxy-4'-methyl-3-biphenylyl)-1-hydroxyiminomethyl]naphthalenecarboxylic acid and 6-[1-(6-Benzyloxy-5-tert-butyl-4'-methyl-3-biphenylyl)-1-hydroxyiminomethyl]naphthalenecarboxylic acid.

According to the present invention, the compounds of formula (I) that are more particularly preferred are those in which:

$R_1$ is (a) or (b), and

X is a radical $CR_{10}R_{11}$.

The present invention also features processes for preparing the compounds of formula (I), in particular according to the reaction schemes in the FIGURE of Drawing.

A general description of the preparation of the compounds of general formulae 6 to 11 is given below.

Compound 4, in the case where R=OR', may be obtained from compound 1 when $R_2$=OR$_2$' by ortho-iodination and O-alkylation (X=I), from compound 2 when $R_2$=NR'R" by ortho-iodination (X=I), and from 3 by conversion of the bromide of 3 into acid or aldehyde after lithiation with butyllithium followed by formylation and formation of the trifluoromethanesulfonyl on the phenol function of the corresponding ester or aldehyde (X=OTf).

In the case where R=Br, 4 is obtained from 3 to O-alkylation or double N-alkylation. The intermediate 5 is prepared, for example, from the iodide function of compound 4 (X=I) or a trifluoromethanesulfonyl function of 4 (X=OTf) by a Suzuki, Stille or Buchwald coupling, respectively, with stannic derivatives or aromatic boronic acids, catalysed with a transition metal complex, for example tetrakis(triphenylphosphinepalladium).

The compounds 5 for which R=COOR' may be converted into acids by saponification, and then into methyl ketones by reaction with methyllithium: the compound 5 in which R=COMe are thus obtained.

When the compounds of general structure 5 are obtained, compounds 6-11 are obtained in the following manner:

The compounds 6 may be obtained by formation of the acids corresponding to the esters 5, followed by conversion of these acids into the acid chlorides thereof, for example by reaction with thionyl chloride. These acid chlorides may then be coupled with organometallic derivatives of naphthylzinc type, or with naphthoic boronic acids, in the presence of catalysts based on transition metals, for example tetrakis (triphenylphosphinepalladium). The precursors of the compounds of general structure 6 are generally obtained in the form of esters: the acids of structure 6 may be obtained by saponification, for example by reaction with sodium hydroxide.

The compounds 7 may be prepared by forming a chalcone bond by reacting the methyl ketone of 7 with a corresponding aromatic aldehyde in the presence of potassium hydroxide.

The compounds of general structure 8 may be prepared from the aldehyde 7 by creating a propargyl alcohol function by adding a propargyl anion, for example by reaction with ethynylmagnesium bromide, followed by Sonogashira coupling with an aromatic halide such as, for example, 4-iodobenzoic acid in the presence of copper salts and a catalyst based on a transition metal complex such as, for example, tetrakis (triphenylphosphinepalladium).

The compounds of general structure 9 may be obtained from the compounds of structure 6, for example after reduction or alkylation of the carbonyl function ($R_3,R_4$=OH, H or alkyl, respectively), or alternatively by reduction followed by a dehydroxylation ($R_3,R_4$=H, H), or acetalization of the carbonyl function ($R_3,R_4$=OR, OR), or formation of an oxime on the carbonyl function of 6 by reaction with a corresponding alkoxylamine or hydroxyl.

The compounds of general structure 10 may be obtained from the compounds of structure 7, for example after reduction or alkylation of the carbonyl function ($R_3,R_4$=OH, H or alkyl, respectively), for example reaction with sodium borohydride or an alkylmagnesium halide.

The compounds of general structure 11 may be prepared from the compounds of structure 8, by oxidation of the benzyl alcohol to a ketone ($R_3$, $R_4$=C=O), for example after reaction with manganese oxide, or oxidation followed by formation of an oxime on the carbonyl function of 8 by reaction with a corresponding alkoxylamine or hydroxyl ($R_3$, $R_4$=C=N—OR), or dehydroxylation of the benzyl alcohol function ($R_3$, $R_4$=H,H), for example by reaction with triethylsilane in the presence of boron trifluoride, or by oxidation and formation of an acetal ($R_3$, $R_4$=OAlk, OAlk), or by oxidation and alkylation of the carbonyl function ($R_3$, $R_4$=Alkyl, OH), for example by addition of an alkylmagnesium halide, or by O-alkylation of the alcohol function of 8 ($R_3$, $R_4$=OAlk, H).

The compounds according to the invention have inhibitory properties on RAR-type receptors. This RAR-receptor inhibitory activity is measured in a test of transactivation by means of the dissociation constant Kdapp (apparent) and the $IC_{50}$ (concentration that inhibits 50% of the reference agonist activity).

According to the invention, the expression "inhibitor of RAR-type receptors" means any compound which, for at least one of the RAR subtypes, has a dissociation constant Kdapp of less than or equal to 1 μm, and an $IC_{50}$ value≦100 nM, in a transactivation test as described in Example 10 below.

The preferred compounds of the present invention have, for at least one of the RAR subtypes, a dissociation constant Kdapp of less than or equal to 500 nM and advantageously less than or equal to 100 nM.

The present invention also features administration of the compounds of formula (I) as described above, as medicinal/therapeutic products.

The compounds according to the invention are particularly suitable in the following regimes or regimens of treatment:

1) for treating dermatological conditions or afflictions associated with a keratinization disorder relating to cell differentiation and proliferation, especially for treating common acne, comedones, polymorphs, acne rosacea, nodulocystic acne, acne conglobata, senile acne, and secondary acnes such as solar acne, medication-related acne or occupational acne;

2) for treating other types of keratinization disorders, especially ichthyosis, ichthyosiform conditions, Darier's disease, palmoplantar keratoderma, leucoplakia and leucoplakiform conditions, and cutaneous or mucous (buccal) lichen;

3) for treating other dermatological conditions or afflictions having an inflammatory immunoallergic component, with or without cell proliferation disorder, and especially all forms of psoriasis, whether cutaneous, mucous or ungual, and even psoriatic rheumatism, or cutaneous atopy, such as eczema, or respiratory atopy, or alternatively gingival hypertrophy;

4) for treating all dermal or epidermal proliferations, whether benign or malignant, and whether of viral origin or otherwise, such as common warts, flat warts and verruciform epidermodysplasia, oral or florid papillomatoses, T lymphoma, and proliferations that may be induced by ultraviolet radiation, especially in the case of basocellular and spinocellular epithelioma, and also any cutaneous precancerous lesion such as keratoacanthomas;

5) for treating other dermatological disorders such as immune dermatoses, such as lupus erythematosus, immune bullous diseases and collagen diseases, such as scleroderma;

6) for the treatment of dermatological or general conditions or afflictions having an immunological component;

7) for treating certain opthalmological disorders, especially corneopathies, 8) for preventing or curing the stigmata of epidermal and/or dermal atrophy induced by local or systemic corticosteroids, or any other form of cutaneous atropy, 9) for the treatment of any cutaneous or general condition or affliction of viral origin, 10) for the treatment of skin disorders caused by exposure to UV radiation, and also for repairing or combating aging of the skin, whether photoinduced or chronological aging, or for reducing pigmentations and actinic keratosis, or any pathology associated with chronological or actinic aging, such as xerosis;

11) for combating sebaceous function disorders, such as the hyperseborrhoea of acne or simple seborrhoea;

12) for preventing or treating cicatrization disorders, or for preventing or repairing stretch marks, or alternatively for promoting cicatrization, 13) for the treatment of pigmentation disorders, such as hyperpigmentation, melasma, hypopigmentation or vitiligo;

14) for the treatment of lipid metabolism conditions or afflictions, such as obesity, hyperlipidaemia, or non-insulin-dependent diabetes;

15) for the treatment of inflammatory conditions or afflictions such as arthritis;

16) for the treatment or prevention of cancerous or precancerous conditions;

17) for the prevention or treatment of alopecia of various origins, especially alopecia caused by chemotherapy or radiation;

18) for the treatment of disorders of the immune system, such as asthma, type I sugar diabetes, multiple sclerosis or other selective dysfunctions of the immune system; and 19) for the treatment of conditions or afflictions of the cardiovascular system, such as arteriosclerosis or hypertension.

The present invention also features pharmaceutical compositions comprising, formulated into a physiologically acceptable medium, at least one compound of formula (I) as defined above.

This invention also features novel medicinal compositions especially suited for treating the abovementioned conditions, disorders or afflictions which are characterized in that they comprise, formulated into a pharmaceutically acceptable support that is compatible with the mode of administration selected for the composition, at least one compound of formula (I), an optical isomer thereof or a salt thereof.

The compositions according to the invention may be administered enterally, parenterally, topically or ocularly. The pharmaceutical composition is preferably packaged in a form that is suitable for topical application.

Via the enteral route, the composition may be in the form of tablets, gel capsules, dragees, syrups, suspensions, solutions, powders, granules, emulsions, suspensions of microspheres or nanospheres or lipid or polymer vesicles allowing a controlled release. Via the parenteral route, the composition may be in the form of solutions or suspensions for infusion or for injection.

The compounds according to the invention are generally administered at a daily dose of about 0.01 mg/kg to 100 mg/kg of body weight, in 1 to 3 dosage intakes.

The compounds are administered systemically, at a concentration generally ranging from 0.001% to 10% by weight and preferably from 0.01% to 1% by weight relative to the weight of the composition.

Via the topical route, the pharmaceutical compositions according to the invention are more particularly suited for treating the skin and mucous membranes and may be in liquid, pasty or solid form, and more particularly in the form or ointments, creams, milks, pomades, powders, impregnated pads, syndets, solutions, gels, sprays, mousses, suspensions, sticks, shampoos or washing bases. They may also be in the form of suspensions of microspheres or nanospheres or of lipid or polymer vesicles or gelled or polymer patches allowing a controlled release.

The compounds are administered topically at a concentration generally ranging from 0.001% to 10% by weight and preferably from 0.01% to 1% by weight, relative to the total weight of the composition.

The compounds of formula (I) according to the invention also find applications in cosmetics, in particular in body and hair hygiene and especially for treating acne-prone skin, for promoting regrowth of the hair or for limiting hair loss, for combating the greasy appearance of the skin or the hair, for protection against the harmful aspects of sunlight or for the treatment of physiologically dry skin, and for preventing and/or combating photoinduced or chronological aging.

This invention thus also features compositions comprising, formulated into a cosmetically acceptable support, at least one of the compounds of formula (I).

The present invention also features the cosmetic use of compositions comprising at least one compound of formula (I) for preventing and/or treating the signs of aging and/or dry skin.

This invention also features the cosmetic use of a composition comprising at least one compound of formula (I) for body or hair hygiene.

The cosmetic compositions according to the invention containing, formulated into a cosmetically acceptable support, at least one compound of formula (I) or an optical or geometrical isomer thereof or a salt thereof, may be especially in the form of a cream, a milk, a gel, suspensions of microspheres or nanospheres or lipid or polymer vesicles, impregnated pads, solutions, sprays, mousses, sticks, soaps, shampoos or washing bases.

The concentration of compound of formula (I) in the cosmetic composition preferably ranges from 0.001% to 3% by weight relative to the total weight of the composition.

The pharmaceutical and cosmetic compositions as described above may also contain inert additives, or even pharmacodynamically active additives as regards the pharmaceutical compositions, or combinations of these additives, and especially:
  wetting agents;
  flavor enhancers;
  preservatives such as para-hydroxybenzoic acid esters;
  stabilizers;
  moisture regulators;
  pH regulators;
  osmotic pressure modifiers;
  emulsifiers;
  UV-A and UV-B screening agents;
  antioxidants such as α-tocopherol, butylhydroxyanisole, butylhydroxytoluene, superoxide dismutase, ubiquinol or certain metal-chelating agents;
  depigmenting agents such as hydroquinone, azelaic acid, caffeic acid or kojic acid;
  emollients;
  moisturizers, for instance glycerol, PEG 400, thiamorpholinone and its derivatives or urea;
  antiseborrhoeic or antiacne agents, such as S-carboxymethylcysteine, S-benzylcysteamine, salts thereof or derivatives thereof, or benzoyl peroxide;
  antibiotics, for instance erythromycin and its esters, neomycin, clindamycin and its esters, and tetracyclines;
  antifungal agents such as ketoconazole or poly-4,5-methylene-3-isothiazolidones;
  agents for promoting regrowth of the hair, for instance Minoxidil (2,4-diamino-6-piperidinopyrimidine 3-oxide) and its derivatives, Diazoxide (7-chloro 3-methyl-1,2,4-benzothiadiazine 1,1-dioxide) and Phenytoin (5,4-diphenylimidazolidine-2,4-dione);
  non-steroidal anti-inflammatory agents;
  carotenoids and especially β-carotene;
  anti-psoriatic agents such as anthralin and its derivatives;
  eicosa-5,8,11,14-tetraynoic acid and eicosa-5,8,11-triynoic acid, and esters and amides thereof;
  retinoids, i.e., natural or synthetic RAR or RXR receptor ligands;
  corticosteroids or oestrogens;
  α-hydroxy acids and α-keto acids or derivatives thereof, such as lactic acid, malic acid, citric acid, glycolic acid, mandelic acid, tartaric acid, glyceric acid or ascorbic acid, and also salts, amides or esters thereof, or β-hydroxy acids or derivatives thereof, such as salicylic acid and its salts, amides or esters;
  ion-channel blockers such as potassium-channel blockers;
  or alternatively, more particularly for pharmaceutical compositions, in combination with medicinal active agents known to interfere with the immune system (for example cyclosporin, FK 506, glucocorticoids, monoclonal antibodies, cytokines or growth factors, etc.).

Needless to say, one skilled in the art will take care to select the optional compound(s) to be added to these compositions such that the advantageous properties intrinsically associated with the present invention are not, or are not substantially, adversely affected by the envisaged addition.

Examples of the production of active compounds of formula (I) according to the invention, biological activity results and also various concrete formulations based on such compounds, will now be given, for illustrative purposes and in nowise limitative. In said examples to follow, all parts and percentages are given by weight, unless otherwise indicated.

EXAMPLE 1

Synthesis of 4-[3-(6-Benzyloxy-5-butyl-4-methyl-3-biphenylyl)-3-hydroxy-1-propynyl]benzoic Acid a. Preparation of 3-tert-Butyl-4-hydroxy-5-iodobenzoic Acid 20 g (103 mmol) of 3-tert-butyl-4-hydroxybenzoic acid are dissolved in 400 mL of methanol. 4.12 g (103 mmol) of sodium hydroxide and 15.4 g (103 mmol) of sodium iodide are added. The reaction medium is cooled to 0° C., and 234 g (113 mmol) of 3.6% sodium hypochlorite are added slowly. The medium is stirred at 0° C. for 2 hours and is then treated with saturated sodium thiosulfate solution. The aqueous phase is acidified and extracted with ethyl ether. A pale yellow solid is obtained (m=24.7 g; yield=75%; m.p.=178° C.).

b. Preparation of Methyl 3-tert-butyl-4-hydroxy-5-iodobenzoate 24.7 g (77 mmol) of 3-tert-Butyl-4-hydroxy-5-iodobenzoic acid are dissolved in 500 mL of methanol and 50 mL of THF. 5 mL of concentrated sulfuric acid are added and the reaction medium is refluxed for 18 hours. The reaction medium is concentrated under reduced pressure and then diluted in a dichloromethane/water mixture. The organic phase is washed with water and then concentrated under reduced pressure. A yellow solid is obtained (m=24.1 g; yield=94%; m.p.=67° C.).

c. Preparation of Methyl 4-benzyloxy-3-tert-butyl-5-iodobenzoate 24.1 g (72 mmol) of methyl 3-tert-butyl-4-hydroxy-5-iodobenzoate are dissolved in 200 mL of dimethylformamide. 3.47 g (86 mmol) of 60% sodium hydride are added slowly and the reaction medium is stirred for 1 hour. 9.4 mL (79 mmol) of benzyl bromide are then added and the medium is stirred at room temperature for 2 hours, and is then hydrolysed and extracted with ethyl ether. The organic phase is washed 3 times with water and then concentrated under reduced pressure. The residue is purified by chromatography (eluent: 98 heptane/2 ethyl acetate). A yellow oil is obtained (m=24.3 g; yield=80%).

d. Preparation of Methyl 6-benzyloxy-5-tert-butyl-4'-methyl-3-biphenylcarboxylate 12 g (28 mmol) of methyl 4-benzyloxy-3-tert-butyl-5-iodobenzoate are dissolved with 5.8 g (42 mmol) of 4-methylbenzeneboronic acid and 12.7 g (84 mmol) of caesium fluoride in 400 mL of dioxane. The reaction medium is degassed with a flow of nitrogen for 15 minutes, and 1.7 g (1.4 mmol) of tetrakis(triphenylphosphine)palladium are then added. The reaction medium is refluxed for 4 hours and then cooled and hydrolysed. After extraction with ethyl acetate, the organic phase is filtered and concentrated. The residue is purified by chromatography (eluent: 98 heptane/2 ethyl acetate): a colorless oil is obtained (m=9 g, yield=83%).

e. Preparation of 6-Benzyloxy-5-tert-butyl-4'-methyl-3-biphenylcarbaldehyde 1 g (2.6 mmol) of methyl 6-benzyloxy-5-tert-butyl-4'-methyl-3-biphenylcarboxylate is dissolved in 40 mL of anhydrous ethyl ether, and the medium is cooled to 0° C. 130 mg (3.3 mmol) of lithium aluminum hydride are added and the reaction medium is stirred for 1 hour. The reaction is hydrolysed by sequential addition of 130 μL of water, 130 μL of 15% sodium hydroxide solution and 400 μL of water. The reaction medium is filtered and the filtrate is concentrated under reduced pressure. The residue obtained is dissolved in 30 mL of dichloromethane, and 2 g (23 mmol) of manganese dioxide are added. The medium is refluxed for 5 hours, and filtered through Celite. A yellow oil is obtained (m=780 mg; yield=85%).

f. Preparation of 1-(6-Benzyloxy-5-tert-butyl-4'-methyl-3-biphenylyl)prop-2-yn-1-ol 780 mg (2.2 mmol) of 6-benzyloxy-5-tert-butyl-4'-methyl-3-biphenylcarbaldehyde are dissolved in 50 mL of THF, and the reaction medium is cooled to 0° C. 5.7 mL (2.8 mmol) of 0.5 M ethynylmagnesium bromide solution are added slowly. The medium is stirred at 0° C. for 2 hours and the reaction is then treated with a saturated ammonium chloride solution. The residue obtained is purified by chromatography on a column of silica (eluent: 9 heptane/1 ethyl acetate). A yellow oil is obtained (m=740 mg; yield=89%).

g. Synthesis of 4-[3-(6-Benzyloxy-5-tert-butyl-4'-methyl-3-biphenylyl)-3-hydroxy-1-propynyl]benzoic Acid 740 mg (1.9 mmol) of 1-(6-Benzyloxy-5-tert-butyl-4'-methyl-3-biphenylyl)prop-2-yn-1-ol are dissolved in 15 mL of triethylamine and 1 mL of dimethylformamide. 390 mg (1.6 mmol) of 4-iodobenzoic acid and 30 mg (0.15 mmol) of copper iodide are added. The medium is degassed with a flow of nitrogen, and 56 mg (0.08 mmol) of bis(triphenylphosphine)dichloropalladium are then added. The reaction medium is stirred for 14 hours at room temperature and then treated with a saturated ammonium chloride solution and extracted with ethyl acetate. The organic phase is washed with 1 N hydrochloric acid solution and then dried and concentrated. The residue obtained is purified by chromatography on a column of silica (eluent: 1 heptane 1 ethyl acetate). The solid obtained is then recrystallized from a heptane/ether mixture. A white solid is obtained (m=270 mg; yield=35%; m.p.=170° C.).

$^1$H NMR/CDCl$_3$+DMSO 1.38 (s, 9H); 2.29 (s, 3H); 4.37 (s, 2H); 5.50 (s, 1H); 5.57 (s, 1H); 7.03 (d, J=6 Hz, 2H); 7.11 (d, J=8 Hz, 2H); 7.17-7.20 (m, 2H); 7.36 (s, 1H); 7.42-7.5 (m, 5H); 7.51 (s, 1H); 7.9 (d, J=8 Hz, 2H).

EXAMPLE 2

Synthesis of 4-[(E)-3-(6-Benzyloxy-5-tert-butyl-4'-methyl-3-biphenylyl)-3-oxopropenyl]benzoic Acid a. Preparation of 1-(6-Benzyloxy-5-tert-butyl-4'-methyl-3-biphenylyl)ethanone 2 g (5.1 mmol) of methyl 6-benzyloxy-5-tert-butyl-4'-methyl-3-biphenylcarboxylate (Example 1,d) are dissolved in 30 mL of THF, 15 mL of methanol and 2 mL of water. 320 mg (7.7 mmol) of lithium hydroxide hydrate are added and the reaction medium is refluxed for 5 hours and then cooled. The medium is neutralized with a 1 N hydrochloric acid solution and the medium is then extracted with ethyl ether. A white powder is obtained (m.p.=196° C.), which is dissolved in 10 mL of ethyl ether and 5 mL of THF. The medium is cooled to −78° C., and 11 mL (11 mmol) of 1 N methyllithium solution are then added dropwise. The medium is stirred at this temperature for 3 hours and is then treated with 5 mL of trimethylsilyl chloride. The medium is hydrolysed with a saturated ammonium chloride solution and then extracted with ethyl ether. The residue obtained is purified by chromatography (eluent: 9 heptane/1 ethyl acetate). A yellow crystalline solid is obtained (m=1.1 g; yield=60%; m.p.=104° C.).

b. Synthesis of 4-[(E)-3-(6-Benzyloxy-5-tert-butyl-4'-methyl-3-biphenylyl)-3-oxopropenyl]benzoic Acid 970 mg (2.6 mmol) of 1-(6-benzyloxy-5-tert-butyl-4'-methyl-3-biphenylyl)ethanone are dissolved in 40 mL of methanol. 350 mg (2.3 mmol) of 4-carboxybenzaldehyde are added, followed by 1.23 mL (10 mmol) of 47% KOH. The reaction medium is stirred for 36 hours and then acidified with concentrated hydrochloric acid. The medium is extracted with ethyl acetate, and the residue obtained is purified by chromatography on a column of silica. The solid obtained is recrystallized from an ethyl ether/heptane mixture. A yellow powder is obtained (m=500 mg; yield=38%; m.p.=208° C.).

$^1$H NMR/CDCl$_3$ 1.50 (s, 9H); 2.42 (s, 3H); 4.55 (s, 2H); 7.13-7.25 (m, 2H); 7.28-7.30 (m, 5H); 7.56 (d, J=8.4 Hz, 2H); 7.66 (d, J=16 Hz, 1H); 7.75 (d, J=8 Hz, 2H); 7.85-7.90 (m, 2H); 8.10 (s, 1H); 8.17 (d, J=8 Hz, 2H).

EXAMPLE 3

Synthesis of 4-[(E)-3-(5-tert-Butyl-6-isobutoxy-4'-methyl-3-biphenylyl)-3-oxopropenyl]benzoic Acid a. Preparation of Methyl 5-tert-butyl-6-hydroxy-4'-methyl-3-biphenylcarboxylate 5.4 g (14 mmol) of methyl 6-benzyloxy-5-tert-butyl-4'-methyl-3-biphenylcarboxylate (Example 1, d) are dissolved in 100 mL of acetonitrile. 6 mL (41 mmol) of trimethylsilyl iodide are added and the mixture is heated at 50° C. for 24 hours. After extraction, the residue obtained is subjected to esterification conditions similar to those of Example 1 b, and the residue obtained is purified by chromatography. A white solid is obtained (m=1.6 g, yield=36%; m.p.=105° C.).

b. Preparation of Methyl 5-tert-butyl-6-isobutoxy-4'-methyl-3-biphenylcarboxylate In a manner similar to that of Example 1c, by reacting 1.57 g (5.3 mmol) of methyl 5-tert-butyl-6-hydroxy-4'-methyl-3-biphenylcarboxylate with 1.14 mL (10.5 mmol) of isobutyl bromide. A yellow oil is obtained (m=1.8 g; yield=95%).

c. Preparation of 1-(5-tert-Butyl-6-isobutoxy-4'-methyl-3-biphenylyl)ethanone In a similar manner to that of Example 2a, by reacting 1.8 g (5.1 mmol) of methyl 5-tert-butyl-6-isobutoxy-4'-methyl-3-biphenylcarboxylate with 330 mg (7.9 mmol) of lithium hydroxide hydrate, followed by reacting the acid obtained (1.2 g; 3.8 mmol) with 11 mL (11 mmol) of 1 M methyllithium solution. A colorless oil is obtained (m=1 g; yield=54%).

d. Synthesis of 4-[(E)-3-(5-tert-Butyl-6-isobutoxy-4'-methyl-3-biphenylyl)-3-oxopropenyl]benzoic Acid In a similar manner to that of Example 2 b, by reacting 1 g (2.9 mmol) of 1-(5-tert-Butyl-6-isobutoxy-4'-methyl-3-biphenylyl)ethanone with 400 mg (2.6 mmol) of 4-carboxybenzaldehyde. A yellow solid is obtained (m=700 mg; yield=50%; m.p.=243° C.).

$^1$H NMR/CDCl$_3$ 0.78 (d, J=8 Hz, 6H); 1.51 (s, 9H); 1.75-1.9 (m, 1H); 2.44 (s, 3H); 3.27 (d, J=4 Hz, 2H); 7.27 (d, J=8 Hz, 2H); 7.46 (d, J=8 Hz, 2H); 7.65 (d, J=16 Hz, 1H); 7.74 (d, J=8 Hz, 2H); 7.82-7.84 (m, 2H); 8.06 (s, 1H); 8.16 (d, J=8 Hz, 2H).

EXAMPLE 4

Synthesis of 4-[(E)-3-(5-tert-Butyl-6-isobutoxy-4'-methyl-3-biphenylyl)-3-hydroxypropenyl]benzoic Acid 440 mg (0.9 mmol) of 4-[(E)-3-(5-tert-butyl-6-isobutoxy-4'-methyl-3-biphenylyl)-3-oxopropenyl]benzoic acid are dissolved in 50 mL of methanol. 450 mg (1.2 mmol) of cerium chloride heptahydrate are added, and the medium is stirred for 30 minutes. 70 mg (1.9 mmol) of sodium borohydride are then added, and the reaction medium is stirred for 15 minutes until completely decolorized, and then treated with a saturated ammonium chloride solution. The residue obtained after extraction with ethyl acetate is purified by chromatography (eluent: 1 heptane/1 ethyl acetate). A white crystalline solid is obtained after recrystallization from a heptane/ethyl acetate mixture (m=180 mg; yield=42%; m.p.=175° C.).

$^1$H NMR/CDCl$_3$+DMSO: 0.71 (d, J=8 Hz, 6H); 1.42 (s, 9H); 1.7 (m, 1H); 2.39 (s, 3H); 3.15 (d, J=8 Hz, 2H); 5.34 (d, J=6 Hz, 1H); 6.53 (d, J=8 Hz, 1H); 6.73 (d, J=12.4 Hz, 1H); 7.16-7.18 (m, 2H); 7.33 (s, 1H); 7.38-7.43 (m, 4H); 7.97 (d, J=8 Hz, 2H).

EXAMPLE 5

Synthesis of 4-[3-Hydroxy-3-(5,5,8,8-tetramethyl-4-p-tolyl-5,6,7,8-tetrahydro-2-naphthyl)-1-propynyl]benzoic Acid a. Preparation of 3-Formyl-5,5,8,8-tetramethyl-5,6,7,8-tetrahydro-1-naphthyl 1,1,1-trifluoromethanesulfonate 6 g (26 mmol) of 4-hydroxy-5,5,8,8-tetramethyl-5,6,7,8-tetrahydro-2-naphthalenecarbaldehyde (Example 16a) are dissolved in 150 mL of dichloromethane. 6.8 mL (39 mmol) of triethylamine are added, followed by dropwise addition of a solution of 10.4 g (29 mmol) of 1,1,1-trifluoro-N-phenyl-N-trifluoromethanesulfonylmethanesulfonamide in 50 mL of dichloromethane. A catalytic amount of dimethylaminopyridine is added and the reaction medium is stirred for 48 hours at room temperature. After the usual treatment with a saturated ammonium chloride solution, the residue obtained is purified by chromatography (eluent: 5 ethyl acetate/95 heptane). A white crystalline solid is obtained (m=8.9 g; yield=94%; m.p.=70° C.).

b. Preparation of 5,5,8,8-Tetramethyl-4-p-tolyl-5,6,7,8-tetrahydro-2-naphthalenecarbaldehyde 1.4 g (3.8 mmol) of 3-formyl-5,5,8,8-tetramethyl-5,6,7,8-tetrahydro-1-naphthyl 1,1,1-trifluoromethanesulfonate are dissolved in 50 mL of DME, followed by 625 mg (4.6 mmol) of p-tolylboronic acid. 485 mg (11.4 mmol) of lithium chloride and 4.6 mL (9.2 mmol) of 2 M potassium carbonate solution are added to the reaction medium, which is then degassed with a flow of nitrogen and then heated to 90° C. 220 mg of tetrakis(triphenylphosphine)palladium are added and the reaction medium is stirred at reflux for 20 hours, then hydrolysed and extracted with ethyl acetate. The residue obtained is purified by chromatography, to give an orange-colored oil (m=980 mg; yield=85%).

c. Preparation of 1-(5,5,8,8-Tetramethyl-4-p-tolyl-5,6,7,8-tetrahydro-2-naphthyl)prop-2-yn-1-ol In a similar manner to that of Example 1 f, by reacting 950 mg (3.1 mmol) of 5,5,8,8-tetramethyl-4-p-tolyl-5,6,7,8-tetrahydro-2-naphthalenecarbaldehyde with 4.5 mL (4.5 mmol) of 1 N ethynylmagnesium bromide solution. A colorless oil is obtained (m=1 g; yield=98%).

d. Synthesis of 4-[3-Hydroxy-3-(5,5,8,8-tetramethyl-4-p-tolyl-5,6,7,8-tetrahydro-2-naphthyl)-1-propynyl]benzoic Acid In a similar manner to that of Example 1g, by reacting 950 mg (2.9 mmol) of 1-(5,5,8,8-tetramethyl-4-p-tolyl-5,6,7,8-tetrahydro-2-naphthyl)prop-2-yn-1-ol with 595 mg (2.4 mmol) of 4-iodobenzoic acid in the presence of 47 mg of copper iodide and 54 mg of bis(triphenylphosphine)dichloropalladium. The desired product is obtained in the form of white crystals (m=1 g; yield=81%; m.p.=207° C.).

$^1$H NMR (DMSO): 1.07 (s, 6H); 1.38 (s, 6H); 1.59-1.61 (m, 2H); 1.73-1.76 (m, 2H); 2.41 (s, 3H); 5.62 (d, J=5.1 Hz, 1H); 6.18 (d, J=5.1 Hz, 1H); 6.91 (s, 1H); 7.18-7.24 (m, 4H); 7.61 (m, 1H); 7.56 (d, J=8.3 Hz, 2H); 7.98 (d, J=8.2 Hz, 2H); 13.4 (bs, 1H).

EXAMPLE 6

Synthesis of 4-3-[4-(4-tert-Butylphenyl)-5,5,8,8-tetramethyl-5,6,7,8-tetrahydro-2-naphthyl]-3-hydroxy-1-propynyl}benzoic Acid a. Preparation of 4-(4-tert-Butylphenyl)-5,5,8,8-tetramethyl-5,6,7,8-tetrahydro-2-naphthalenecarbaldehyde In a manner similar to that of Example 21 b, by reacting 5 g (14 mmol) of 3-formyl-5,5,8,8-tetramethyl-5,6,7,8-tetrahydro-1-naphthyl 1,1,1-trifluoromethanesulfonate (Example 21a) with 2.85 g (16 mmol) of 4-tert-butylphenylboronic acid, in the presence of 1.17 g (28 mmol) of lithium chloride, 16 mL (32 mmol) of 2 M potassium carbonate solution and 800 mg of tetrakis(triphenylphosphine)palladium. The product is obtained in the form of white crystals (m=3.1 g; yield=65%, m.p.=129° C.).

b. Preparation of 1-[4-(4-tert-Butylphenyl)-5,5,8,8-tetramethyl-5,6,7,8-tetrahydro-2-naphthyl]prop-2-yn-1-ol In a manner similar to that of Example 1f, by reacting 350 mg (1 mmol) of 4-(4-tert-butylphenyl)-5,5,8,8-tetramethyl-5,6,7,8-tetrahydro-2-naphthalenecarbaldehyde with 2.6 mL (1.3 mmol) of 0.5 N ethynylmagnesium bromide solution. White crystals are obtained (m=300 mg; yield=80%).

c. Synthesis of 4-[3-Hydroxy-3-(5,5,8,8-tetramethyl-4-p-tolyl-5,6,7,8-tetrahydro-2-naphthyl)prop-1-ynyl]benzoic Acid In a similar manner to that of Example 1g, by reacting 300 mg (0.8 mmol) of 1-[4-(4-tert-butylphenyl)-5,5,8,8-tetramethyl-5,6,7,8-tetrahydro-2-naphthyl]prop-2-yn-1-ol with 166 mg (0.7 mmol) of 4-iodobenzoic acid in the presence of 7 mg of copper iodide and 12 mg of bis(triphenylphosphine)dichloropalladium. The desired product is obtained in the form of white crystals (m=280 mg; yield=72%; m.p.=180° C.).

$^1$H NMR (DMSO) 1.02 (s, 6H); 1.33 (m, 15H); 1.55 (m, 2H); 1.68 (m, 2H); 5.55 (s, 1H); 6.10 (s, 1H); 6.85 (d, 1H, 4 Hz); 7.18 (d, 2H, 1.6 Hz); 7.38 (d, 2H, 8.4 Hz); 7.50 (d, 2H, 8 Hz); 7.54 (d, 1H, 2 Hz); 7.91 (d, 2H, 8 Hz).

EXAMPLE 7

Synthesis of 4-(E)-3-Oxo-3-(5,5,8,8-tetramethyl-4-p-tolyl-5,6,7,8-tetrahydro-2-naphthyl)propenyl]benzoic Acid a. Preparation of 3-Acetyl-5,5,8,8-tetramethyl-5,6,7,8-tetrahydro-1-naphthyl 1,1,1-trifluoromethanesulfonate In a manner similar to that of Example 21a, by reacting 8.2 g (33 mmol) of 1-(4-hydroxy-5,5,8,8-tetramethyl-5,6,7,8-tetrahydro-2-naphthyl)ethanone (Example 20a) with 13 g (36 mmol) of 1,1,1-trifluoro-N-phenyl-N-trifluoromethanesulfonylmethanesulfonamide and 8.7 mL (50 mmol) of diisopropylethylamine. A white solid is obtained (m=11.2 g; yield=90%).

b. Preparation of 1-(5,5,8,8-Tetramethyl-4-p-tolyl-5,6,7,8-tetrahydro-2-naphthyl)ethanone In a manner similar to that of Example 21 b, by reacting 1.4 g (3.7 mmol) of 3-acetyl-5,5,8,8-tetramethyl-5,6,7,8-tetrahydro-1-naphthyl 1,1,1-trifluoromethanesulfonate with 625 mg (4.6 mmol) of p-tolylboronic acid, 485 mg (11.4 mmol) of lithium chloride, 4.6 mL (9.2 mmol) of a 2 M potassium carbonate solution and 220 mg of tetrakis(triphenylphosphine)palladium. The desired product is obtained in the form of white crystals (m=830 mg; yield=70%; m.p.=102° C.).

c. Synthesis of 4-[(E)-3-Oxo-(5,5,8,8-tetramethyl-4-p-tolyl-5,6,7,8-tetrahydro-2-naphthyl)propenyl]benzoic Acid In a similar manner to that of Example 2b, by reacting 770 mg (2.4 mmol) of 1-(5,5,8,8-tetramethyl-4-p-tolyl-5,6,7,8-tetrahydro-2-naphthyl)ethanone with 320 mg (2.2 mmol) of 4-carboxybenzaldehyde and 1.2 mL (10 mmol) of 47% KOH. The desired product is obtained in the form of white crystals (m=780 mg; yield=72%; m.p.=242° C.).

$^1$H NMR (CDCl$_3$): 1.10 (s, 6H); 1.42 (s, 6H); 1.61-1.64 (m, 2H); 1.74-1.77 (m, 2H); 2.43 (s, 3H); 7.20-7.22 (m, 4H); 7.43 (s, 1H); 7.54 (d, J=15.7 Hz, 1H); 7.68 (d, J=8.4 Hz, 2H); 7.80 (d, J=15.7 Hz, 1H); 8.07 (s, 1H); 8.11 (d, J=8.4 Hz, 2H).

EXAMPLE 8

Synthesis of 4-{(E)-3-[4-(4-tert-Butylphenyl)-5,5,8,8-tetramethyl-5,6,7,8-tetrahydro-2-naphthyl]-3-oxopropenyl}benzoic Acid a. Preparation of 1-[4-(4-tert-Butylphenyl)-5,5,8,8-tetramethyl-5,6,7,8-tetrahydro-2-naphthyl]ethanone In a manner similar to that of Example 2 b, by reacting 1.3 g (3.4 mmol) of 3-acetyl-5,5,8,8-tetramethyl-5,6,7,8-tetrahydro-1-naphthyl 1,1,1-trifluoromethanesulfonate with 600 mg (4.4 mmol) of 4-tert-butylphenylboronic acid, 450 mg (10.8 mmol) of lithium chloride, 4.6 mL (9.2 mmol) of 2 M potassium carbonate solution and 220 mg of tetrakis(triphenylphosphine)palladium. The desired product is obtained in the form of white crystals (m=812 mg; yield=66%; m.p.=134° C.).

b. Synthesis of 4-[(E)-3-[4-(4-tert-Butylphenyl)-5,5,8,8-tetramethyl-5,6,7,8-tetrahydro-2-naphthyl]-3-oxopropenyl]benzoic Acid In a manner similar to that of Example 2b, by reacting 710 mg (2.0 mmol) of 1-[4-(4-tert-butylphenyl)-5,5,8,8-tetramethyl-5,6,7,8-tetrahydro-2-naphthyl]ethanone with 260 mg (1.8 mmol) of 4-carboxybenzaldehyde and 1.0 mL (8 mmol) of 47% KOH. The desired product is obtained in the form of white crystals (m=590 mg; yield=61%; m.p.=241° C.).

$^1$H NMR (CDCl$_3$): 1.02 (s, 6H); 1.32 (s, 9H); 1.37 (s, 6H); 1.54-1.57 (m, 2H); 1.68-1.71 (m, 2H); 7.15-7.17 (m, 2H); 7.31 (d, J=8.3 Hz, 1H); 7.38 (s, 1H); 7.48 (d, J=15.7 Hz, 1H), 7.63 (d, J=8.5 Hz, 2H); 7.73 (d, J=15.7 Hz, 1H); 8.00 (s, 1H); 8.04 (d, J=8.5 Hz, 2H).

EXAMPLE 9

Synthesis of 4-[(E)-3-Hydroxy-3-(5,5,8,8-tetramethyl-4-p-tolyl-5,6,7,8-tetrahydro-2-naphthyl)propenyl]benzoic Acid In a manner similar to that of Example 4a, by reacting 400 mg (0.88 mmol) of 4-[(E)-3-oxo-3-(5,5,8,8-tetramethyl-4-p-tolyl-5,6,7,8-tetrahydro-2-naphthyl)propenyl]benzoic acid (Example 23) with 428 mg of cerium chloride heptahydrate and 40 mg of sodium borohydride. The desired product is obtained in the form of a white solid (m=200 mg; yield=50%; m.p.=179° C.).

$^1$H NMR (CDCl$_3$): 1.05 (s, 6H); 1.36 (s, 6H); 1.56-1.58 (m, 2H); 1.70-1.72 (m, 2H); 2.38 (s, 3H); 5.26 (d, J=7 Hz, 1H); 6.51 (dd, J1=15.8 Hz, J2=6 Hz, 1H); 6.72 (d, J=15.8 Hz, 1H); 6.82 (s, 1H); 7.10-7.15 (m, 4H); 7.43 (s, 1H); 7.43-7.59 (m, 3H); 8.25 (bs, 2H).

EXAMPLE 10

Transactivation Test

The activation of receptors with an agonist (activator) in HeLa cells leads to the expression of a reporter gene, luciferase, which, in the presence of a substrate, generates light. The activation of the receptors may thus be measured by quantifying the luminescence produced after incubating the cells in the presence of a reference agonist. The inhibitory products displace the agonist from its site, thus preventing activation of the receptor. The activity is measured by quantifying the reduction in light produced. This measurement makes it possible to determine the inhibitory activity of the compounds according to the invention.

Determination of the Kdapp:

In this study, a constant is determined which represents the affinity of the molecule for the receptor. Since this value can fluctuate depending on the basal activity and the expression of the receptor, it is referred to as the Kd apparent (KdApp).

To determine this constant, "crossed curves" of the test product against a reference agonist, 4-[2-(5,5,8,8-tetramethyl-5,6,7,8-tetrahydro-2-naphthyl)propenyl]benzoic acid, are performed in 96-well plates. The test product is used at 10 concentrations and the reference agonist at 7 concentrations. In each well, the cells are in contact with a concentration of the test product and a concentration of the reference agonist, 4-[2-(5,5,8,8-tetramethyl-5,6,7,8-tetrahydro-2-naphthyl) propenyl]benzoic acid. Measurements are also taken for the total agonist (4-[2-(5,5,8,8-tetramethyl-5,6,7,8-tetrahydro-2-naphthyl)propenyl]benzoic acid) and inverse agonist, 4-{(E)-3-[4-(4-tert-butylphenyl)-5,5,8,8-tetramethyl-5,6,7,8-tetrahydro-2-naphthyl]-3-oxopropenyl}benzoic acid, controls.

These crossed curves make it possible to determine the $AC_{50}$ values (concentration at which 50% activation is observed) for the reference ligand at various concentrations of test product. These $AC_{50}$ values are used to calculate the Schild regression by plotting a straight line corresponding to the Schild equation ("*quantition in receptor pharmacology*" Terry P. Kenakin, *Receptors and Channels*, 2001,7,371-385).

In the case of an antagonist, an $IC_{50}$ value (concentration that inhibits 50% of the activity) is calculated by plotting the curve of the product at the concentration of the reference ligand that gives 80% activation.

The HeLa cell lines used are stable transfectants containing the plasmids ERE-βGlob-Luc-SV-Neo (reporter gene) and RAR (α, β, γ) ER-DBD-puro. These cells are inoculated into 96-well plates at a rate of 10 000 cells per well in 100 μl of DMEM medium without phenol red, and supplemented with 10% defatted calf serum. The plates are then incubated at 37° C. and 7% $CO_2$ for 4 hours.

The various dilutions of the test products, of the reference ligand (4-[2-(5,5,8,8-tetramethyl-5,6,7,8-tetrahydro-2-naphthyl)propenyl]benzoic acid), of the 100% control (100 nM 4-[2-(5,5,8,8-tetramethyl-5,6,7,8-tetrahydro-2-naphthyl) propenyl]benzoic acid) and of the 0% control (500 nM 4-{(E)-3-[4-(4-tert-butylphenyl)-5,5,8,8-tetramethyl-5,6,7,8-tetrahydro-2-naphthyl]-3-oxopropenyl}benzoic acid) are added at a rate of 5 μl per well. The plates are then incubated for 18 hours at 37° C. and 7% $CO_2$.

The culture medium is removed by turning over and 100 μl of a 1:1 PBS/luciferine mixture is added to each well. After 5 minutes, the plates are read using the luminescence detector.

| | RAR ALPHA | | RAR BETA | | RAR GAMMA | |
|---|---|---|---|---|---|---|
| | $IC_{50}$ (nM) | Kd app (nM) | $IC_{50}$ (nM) | Kd app (nM) | $IC_{50}$ (nM) | Kd app (nM) |
| Ex. 9 | 437.5 | 250 | 800 | 500 | 75 | 30 |
| Ex. 8 | 3.5 | 2 | 6.4 | 4 | 0.625 | 0.25 |
| Ex. 5 | 7000 | 4000 | 96 | 60 | 37.5 | 15 |
| Ex. 7 | 1.75 | 1 | 0.4 | 0.25 | 2.5 | 1 |

The results obtained with the compounds according to the invention clearly show Kd app values ≦100 nM and an $IC_{50}$ value ≦100 nM for at least one of the receptor subtypes, this clearly demonstrating a reduction in the signal, and in the luminescence in the presence of the reference agonist. The compounds according to the invention are thus clearly inhibitors of retinoic acid receptors (RAR).

EXAMPLE 11

Formulation Examples

This example illustrates various specific formulations based on the compounds according to the invention.

A—Enteral Route:

(a) 0.2 g tablet:

| | |
|---|---|
| Compound of Example 6 | 0.001 g |
| Starch | 0.114 g |
| Dicalcium phosphate | 0.020 g |
| Silica | 0.020 g |
| Lactose | 0.030 g |
| Talc | 0.010 g |
| Magnesium stearate | 0.005 g |

(b) Drinkable suspension in 5 ml ampules:

| | |
|---|---|
| Compound of Example 7 | 0.001 g |
| Glycerol | 0.500 g |
| 70% sorbitol | 0.500 g |
| Sodium saccharinate | 0.010 g |
| Methyl para-hydroxybenzoate | 0.040 g |
| Flavoring | qs |
| Purified water | qs 5 ml |

(c) 0.8 g tablet:

| | |
|---|---|
| Compound of Example 9 | 0.500 g |
| Pregelatinized starch | 0.100 g |
| Microcrystalline cellulose | 0.115 g |
| Lactose | 0.075 g |
| Magnesium stearate | 0.010 g |

(d) Drinkable suspension in 10 ml ampules:

| | |
|---|---|
| Compound of Example 2 | 0.200 g |
| Glycerol | 1.000 g |
| 70% sorbitol | 1.000 g |
| Sodium saccharinate | 0.010 g |
| Methyl para-hydroxybenzoate | 0.080 g |
| Flavoring | qs |
| Purified water | qs 10 ml |

B—Parenteral Route:

(a) Composition:

| | |
|---|---|
| Compound of Example 3 | 0.002 g |
| Ethyl oleate | qs 10 g |

(b) Composition:

| | |
|---|---|
| Compound of Example 1 | 0.05% |
| Polyethylene glycol | 20% |
| 0.9% NaCl solution | qs 100 |

(c) Composition:

| | |
|---|---|
| Compound of Example 3 | 2.5% |
| Polyethylene glycol 400 | 20% |
| 0.9% NaCl solution | qs 100 |

(d) Injectable cyclodextrin composition:

| | |
|---|---|
| Compound of Example 3 | 0.1 mg |
| β-Cyclodextrin | 0.10 g |
| Water for injection | qs 10.00 g |

C—Topical Route:

(a) Ointment:

| | |
|---|---|
| Compound of Example 2 | 0.020 g |
| Isopropyl myristate | 81.700 g |
| Liquid petroleum jelly fluid | 9.100 g |
| Silica ("Aerosil 200" sold by Degussa) | 9.180 g |

(b) Ointment:

| | |
|---|---|
| Compound of Example 5 | 0.300 g |
| White petroleum jelly codex | qs 100 g |

(c) Nonionic water-in-oil cream:

| | |
|---|---|
| Compound of Example 4 | 0.100 g |
| Mixture of emulsifying lanolin alcohols, waxes and oils ("Anhydrous Eucerin" sold by BDF) | 39.900 g |
| Methyl para-hydroxybenzoate | 0.075 g |
| Propyl para-hydroxybenzoate | 0.075 g |
| Sterile demineralized water | qs 100 g |

(d) Lotion:

| | |
|---|---|
| Compound of Example 9 | 0.100 g |
| Polyethylene glycol (PEG 400) | 69.900 g |
| 95% ethanol | 30.000 g |

(e) Hydrophobic ointment:

| | |
|---|---|
| Compound of Example 2 | 0.300 g |
| Isopropyl myristate | 36.400 g |
| Silicone oil ("Rhodorsil 47 V 300" sold by Rhône-Poulenc) | 36.400 g |
| Beeswax | 13.600 g |
| Silicone oil ("Abil 300 000 cst" sold by Goldschmidt) | qs 100 g |

(f) Nonionic oil-in-water cream:

| | |
|---|---|
| Compound of Example 6 | 1.000 g |
| Cetyl alcohol | 4.000 g |
| Glyceryl monostearate | 2.500 g |
| PEG-50 stearate | 2.500 g |
| Karite butter | 9.200 g |
| Propylene glycol | 2.000 g |
| Methyl para-hydroxybenzoate | 0.075 g |
| Propyl para-hydroxybenzoate | 0.075 g |
| Sterile demineralized water | qs 100 g |

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A biaryl compound having the structural formula:

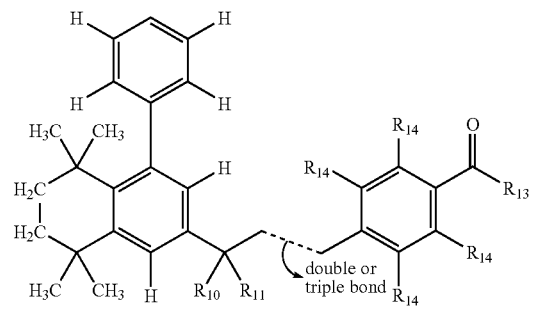

$R_{10}$ and $R_{11}$ are H or OH, or $R_{10}$ and $R_{11}$ together represent a CO radical wherein
$R_{13}$ is a hydroxyl, alkoxy, monoalkylamino or dialkylamino group;
$R_{14}$ is a hydrogen atom, a hydroxyl group or amino group; and the para-position of the benzene ring bonded to the 1,2,3,4-tetrahydro-1,1,4,4-terramethylnaphthalene is optionally substituted with a linear or branched alkyl radical having from 1 to 6 carbon atoms, an alkoxy radical, a monoalkylamino radical, a dialkylamino radical or a halogen atom,
or a salt, isomer or mixture thereof.

2. The biaryl compound as defined by claim 1, wherein the bond represented by the dashed line is a double bond.

3. The biaryl compound as defined by claim 1, wherein the bond represented by the dashed line is a triple bond.

4. The biaryl compound as defined by claim 1, wherein the para-position of the benzene ring bonded to the 1,2,3,4-tetrahydro-1,1,4,4-terramethylnaphthalene is optionally substituted with an alkyl, alkyl amino or alkyloxy group.

5. A salt of the biaryl compound (I) as defined by claim 1.

6. An alkali or alkaline-earth or zinc or organic amine salt of the biaryl compound (I) as defined by claim 1.

7. The biaryl compound as defined by claim 1, containing at least one alkyl radical selected from the group consisting of methyl, ethyl, propyl, isopropyl, butyl, tert-butyl, pentyl and hexyl radicals.

8. The biaryl compound as defined by claim 1, containing at least one fluorine, chlorine and/or bromine atom.

9. The biaryl compound as defined by claim 1, containing at least one alkoxy radical selected from the group consisting of methoxy, ethoxy, propyloxy, isopropoxy, butoxy, tert-butoxy, pentoxy and hexyloxy radicals.

10. The biaryl compound as defined by claim 1, selected from the group consisting of:
4-[3-Hydroxy-3-(5,5,8,8-tetramethyl-4-p-tolyl-5,6,7,8-tetrahydro-2-naphthyl)-1-propynyl]benzoic acid,
4-{3-[4-(4-tert-Butylphenyl)-5,5,8,8-tetramethyl-5,6,7,8-tetrahydro-2-naphthyl]-3-hydroxy-1-propynyl}benzoic acid,
4-{(E)-3-[4-(4-tert-Butylphenyl)-5,5,8,8-tetramethyl-5,6,7,8-tetrahydro-2-naphthyl]-3-oxopropenyl}benzoic acid,
4-[(E)-3-Oxo-3-(5,5,8,8-tetramethyl-4-p-tolyl-5,6,7,8-tetrahydro-2-naphthyl)propenyl]benzoic acid,
4-[(E)-3-Hydroxy-3-(5,5,8,8-tetramethyl-4-p-tolyl-5,6,7,8-tetrahydro-2-naphthyl)propenyl]benzoic acid;
4-{(E)-3-[4-(4-tert-Butylphenyl)-5,5,8,8-tetramethyl-5,6,7,8-tetrahydro-2-naphthyl]-3-hydroxyprapenyl}-2-hydroxybenzoic acid,
4-{(E)-3-[4-(4-tert-Butylphenyl)-5,5,8,8-tetramethyl-5,6,7,8-tetrahydro-2-naphthyl]-3-oxopropenyl}-2-hydroxybenzoic acid,
4-{3-[4-(4-tert-Butylphenyl)-5,5,8,8-tetramethyl-5,6,7,8-tetrahydro-2-naphthyl]-3-hydroxy-1-propynyl}-2-hydroxybenzoic acid,
2-Hydroxy-4-[(E)-3-hydroxy-3-(5,5,8,8-tetramethyl-4-p-tolyl-5,6,7,8-tetrahydro-2-naphthyl)propenyl]benzoic acid,
2-Hydroxy-4-[(E)-3-oxo-3-(5,5,8,8-tetramethyl-4-p-tolyl-5,6,7,8-tetrahydro-2-naphthyl)propenyl]benzoic acid,
2-Hydroxy-4-[3-hydroxy-3-(5,5,8,8-tetramethyl-4-p-tolyl-5,6,7,8-tetrahydro-2-naphthyl)-1-propynyl]benzoic acid,
4-{(E)-3-[4-(4-Dimethylaminophenyl)-5,5,8,8-tetramethyl-5,6,7,8-tetrahydro-2-naphthyl]-3-hydroxypropenyt}benzoic acid, 4-{(E)-3-[4-(4-Dimethylaminophenyl)-5,5,8,8-tetramethyl-5,6,7,8-tetrahydro-2-naphthyl]-3-oxopropenyl}benzoic acid, 4-{3-[4-(4-Dimethylaminophenyl)-5,5,8,8-tetramethyl-5,6,7,8-tetrahydro-2-naphthyl]-3-hydroxy-1-propynyl}benzoic acid, 4-{(E)-3-[4-(4-Dimethylaminophenyl)-5,5,8,8-tetramethyl-5,6,7,8-tetrahydro-2-naphthyl]-3-hydroxypropenyl}-2-hydroxybenzoic acid, 4-{(E)-3-[4-(4-Dimethylaminophenyl)-5,5,8,8-tetramethyl-5,6,7,8-tetrahydro-2-naphthyl]-3-oxopropenyl}-2-hydroxybenzoic acid, 4-{3-[4-(4-Dimethylaminophenyl)-5,5,8,8-tetramethyl-5,6,7,8-tetrahydro-2-naphthyl]-3-hydroxy-1-propynyl}-2-hydroxybenzoic acid, 4-{(E)-3-[4-(4-Diethylaminophenyl)-5,5,8,8-tetramethyl-5,6,7,8-tetrahydro-2-naphthyl]-3-hydroxypropenyl}benzoic acid, 4-{(E)-3-[4-(4-Diethylaminophenyl)-5,5,8,8-tetramethyl-5,6,7,8-tetrahydro-2-naphthyl]-3-oxopropenyl}benzoic acid, 4-{3-[4-(4-Diethylaminophenyl)-5,5,8,8-tetramethyl-5,6,7,8-tetrahydro-2-naphthyl]-3-hydroxy-1-propynyl}benzoic acid, 4-{(E)-3-[4-(4-Diethylaminophenyl)-5,5,8,8-tetramethyl-5,6,7,8-tetrahydro-2-naphthyl]-3-hydroxypropenyl}-2-hydroxybenzoic acid, 4-{(E)-3-[4-(4-Diethylaminophenyl)-5,5,8,8-tetramethyl-5,6,7,8-tetrahydro-2-naphthyl]-3-oxopropenyl}-2-hydroxybenzoic acid, 4-{3-[4-(4-Diethylaminophenyl)-5,5,8,8-tetramethyl-5,6,7,8-tetrahydro-2-naphthyl]-3-hydroxy-1-propynyl}-2-hydroxybenzoic acid, 4-{(E)-3-[4-(4-Methoxyphenyl)-5,5,8,8-tetramethyl-5,6,7,8-tetrahydro-2-naphthyl]-3-hydroxypropenyl}benzoic acid, 4-{(E)-3-[4-(4-Methoxyphenyl)-5,5,8,8-tetramethyl-5,6,7,8-tetrahydro-2-naphthyl]-3-oxopropenyl}benzoic acid, 4-{3-[4-(4-Methoxyphenyl)-5,5,8,8-tetramethyl-5,6,7,8-tetrahydro-2-naphthyl]-3-hydroxy-1-propynyl}benzoic acid, 4-{(E)-3-[4-(4-Methoxyphenyl)-5,5,8,8-tetramethyl-5,6,7,8-tetrahydro-2-naphthyl]-3-hydroxypropenyl}-2-hydroxybenzoic acid, 4-{(E)-3-[4-(4-Methoxyphenyl)-5,5,8,8-tetramethyl-5,6,7,8-tetrahydro-2-naphthyl]-3-oxopropenyl}-2-hydroxybenzoic acid, 4-{3-[4-(4-Methoxyphenyl)-5,5,8,8-tetramethyl-5,6,7,8-tetrahydro-2-naphthyl]-3-hydroxy-1-propynyl}-2-hydroxybenzoic acid, and mixtures thereof.

11. A pharmaceutical composition comprising a therapeutically effective amount of at least one biaryl compound as defined by claim 1, or salt or isomer thereof, formulated into a physiologically acceptable medium therefor.

12. The pharmaceutical composition as defined by claim 11, said at least one biaryl compound, or salt or isomer, comprising from 0.001% to 10% by weight thereof.

13. The pharmaceutical composition as defined by claim 11, said at least one biaryl compound, or salt or isomer, comprising from 0.01% to 1% by weight thereof.

14. A cosmetic composition comprising a cosmetic effective amount of at least one biaryl compound as defined by claim 1, or salt or isomer thereof, formulated into a cosmetically acceptable medium therefor.

15. The cosmetic composition as defined by claim 14, said at least one biaryl compound, or salt or isomer, comprising from 0.001% to 3% by weight thereof.

16. The pharmaceutical composition as defined by claim 11, formulated as a paste, an ointment, a cream, a milk, a pomade, a powder, an impregnated pad, a syndet, a gel, a spray, a mousse, a stick, a shampoo, microspheres, nanospheres, lipid or polymer vesicles, a controlled release patch, a syrup, tablets, capsules, granules, an emulsion, or a dragee.

* * * * *

UNITED STATES PATENT AND TRADEMARK OFFICE
CERTIFICATE OF CORRECTION

| | | |
|---|---|---|
| PATENT NO. | : 7,468,457 B2 | Page 1 of 1 |
| APPLICATION NO. | : 10/991510 | |
| DATED | : December 23, 2008 | |
| INVENTOR(S) | : Thibaud Biadatti et al. | |

It is certified that error appears in the above-identified patent and that said Letters Patent is hereby corrected as shown below:

On the Title page, the Related U.S. Application Data section is incomplete:

It should read:

--Related U.S. Application Data

(63)  Continuation of application No. PCT/EP03/05554, filed on May 27, 2003.

(60)  Provisional application No. 60/387,448, filed on June 11, 2002.--

Signed and Sealed this
Fifteenth Day of December, 2015

Michelle K. Lee
*Director of the United States Patent and Trademark Office*